US008852504B2

(12) United States Patent
Suslick et al.

(10) Patent No.: US 8,852,504 B2
(45) Date of Patent: Oct. 7, 2014

(54) APPARATUS AND METHOD FOR DETECTING AND IDENTIFYING MICROORGANISMS

(75) Inventors: Kenneth S. Suslick, Champaign, IL (US); Matthew J. Placek, Arlington Heights, IL (US); William B. McNamara, III, Champaign, IL (US); Avijit Sen, Champaign, IL (US); James R. Carey, Champaign, IL (US); Jennifer B. Wilson, Cincinnati, OH (US); Crystal K. Keso, Rochester, MN (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1445 days.

(21) Appl. No.: 11/870,670

(22) Filed: Oct. 11, 2007

(65) Prior Publication Data

US 2008/0199904 A1     Aug. 21, 2008

Related U.S. Application Data

(60) Provisional application No. 60/829,025, filed on Oct. 11, 2006.

(51) Int. Cl.
| | |
|---|---|
| *G01N 31/22* | (2006.01) |
| *G01N 31/00* | (2006.01) |
| *C12Q 1/04* | (2006.01) |
| *C12Q 1/00* | (2006.01) |

(52) U.S. Cl.
CPC . *C12Q 1/04* (2013.01); *G01N 31/22* (2013.01)
USPC .............................. 422/50; 422/400; 422/430

(58) Field of Classification Search
CPC .............. C12Q 1/04; C12Q 1/00; C12M 1/34
USPC .................................... 422/103, 50, 400, 430
See application file for complete search history.

(56) References Cited

U.S. PATENT DOCUMENTS

| | | | |
|---|---|---|---|
| 4,264,728 A | 4/1981 | Wilkins | |
| 4,297,173 A | 10/1981 | Hikuma et al. | |
| 5,094,955 A | 3/1992 | Calandra et al. | |

(Continued)

FOREIGN PATENT DOCUMENTS

| | | | | |
|---|---|---|---|---|
| EP | 286307 A2 * | 10/1988 | ............. | G01N 27/12 |
| WO | WO 2004/770035 | * 9/2004 | ............. | G01N 21/64 |

OTHER PUBLICATIONS

Fredericks, M.D, D.N.; Fiedler, B.S. T.L.; Marrazzo, M.D., M.P.H., J.M.; "Molecular Identification of Bacteria Associated with Bacterial Vaginosis." The New England Journal of Medicine, 2005, 353, pp. 1899-1911.*

(Continued)

*Primary Examiner* — Christine T Mui
(74) *Attorney, Agent, or Firm* — Licata & Tyrrell P.C.

(57) ABSTRACT

The present invention is an apparatus for detecting the presence, quantity and identity of one or more microorganisms in a sample and a method for using the same. The apparatus is composed of one or more chambers and a sensing element for sensing microorganisms. In particular embodiments, the sensing element is an array of chemoresponsive dyes deposited on a substrate in a predetermined pattern combination, wherein the combination of the dyes have a distinct and direct spectroscopic, transmission, or reflectance response to distinct analytes produced by the microorganism which is indicative of the presence, quantity and identity of the microorganism.

11 Claims, 12 Drawing Sheets

(56) References Cited

U.S. PATENT DOCUMENTS

| | | | |
|---|---|---|---|
| 5,795,773 A * | 8/1998 | Read et al. | 435/287.5 |
| 5,807,701 A * | 9/1998 | Payne et al. | 435/34 |
| 5,856,175 A | 1/1999 | Thorpe et al. | |
| 5,912,115 A | 6/1999 | Hyman et al. | |
| 5,976,827 A | 11/1999 | Jeffrey et al. | |
| 6,030,822 A | 2/2000 | Lechner et al. | |
| 6,197,577 B1 | 3/2001 | Jeffrey et al. | |
| 6,368,558 B1 * | 4/2002 | Suslick et al. | 422/55 |
| 6,495,102 B1 | 12/2002 | Suslick et al. | |
| 6,627,394 B2 * | 9/2003 | Kritzman et al. | 435/4 |
| 6,777,226 B2 | 8/2004 | Jeffrey et al. | |
| 6,855,514 B2 | 2/2005 | Ogawa | |
| 7,183,073 B2 | 2/2007 | Hyman et al. | |
| 2005/0170497 A1 | 8/2005 | Carr | |

OTHER PUBLICATIONS

Gibson et al., "Detection and simultaneous identification of microoorganisms from headspace samples using an electronic nose", Sensors and Actuators B 1997 44:413-422.

Ivnitski et al., "Biosensors for detection of pathogenic bacteria", Biosensors & Bioelectronics 1999 24:599-624.

Lai et al., "Identification of Upper Respiratory Bacterial Pathogens With the Electronic Nose", Th Lryngoscope 2002 112:975-979.

McEntegart et al., "Detection and discrimination of coliform bacteria with gas sensor arrays", Sensors and Actuators B 2000 70:170-176.

Rakow et al., "A colorimetric sensor array for odour visualization", Nature 2000 406:710-713.

Rakow et al., "Molecular Recognition and Discrimination of Amines with a Colorimetric Array", Angew. Chem. Int. Ed. 2005 44:4528-4532.

Suslick et al., "Colorimetric sensor arrays for molecular recognition", Tetrahedron 2004 60:1113-11138.

Suslick, Kenneth S., "An Optoelectronic Nose: "Seeing" Smells by means of Colorimetric Sensor Arrays", MRS Bulletin 2004 720-725.

Zhang et al., "A Colorimetric Sensor Array for Organics in Water", J. Am. Chem. Soc. 2005 127:11548-11549.

Suslick et al., 2001 Artificial Chemical Sensing: Olfactiobn and the Electronic Nose; Stetter & Penrose, Eds.; Electrochem. Soc.: Pennington, NJ; pp. 8-14—In view of the voluminous nature of this publication and the likelihood that the Examiner may have a copy available to him or her, a copy has not been included herewith. However, if the Examiner does not have a copy available, Applicant will endeavor to supply one at the Examiner's request.

* cited by examiner

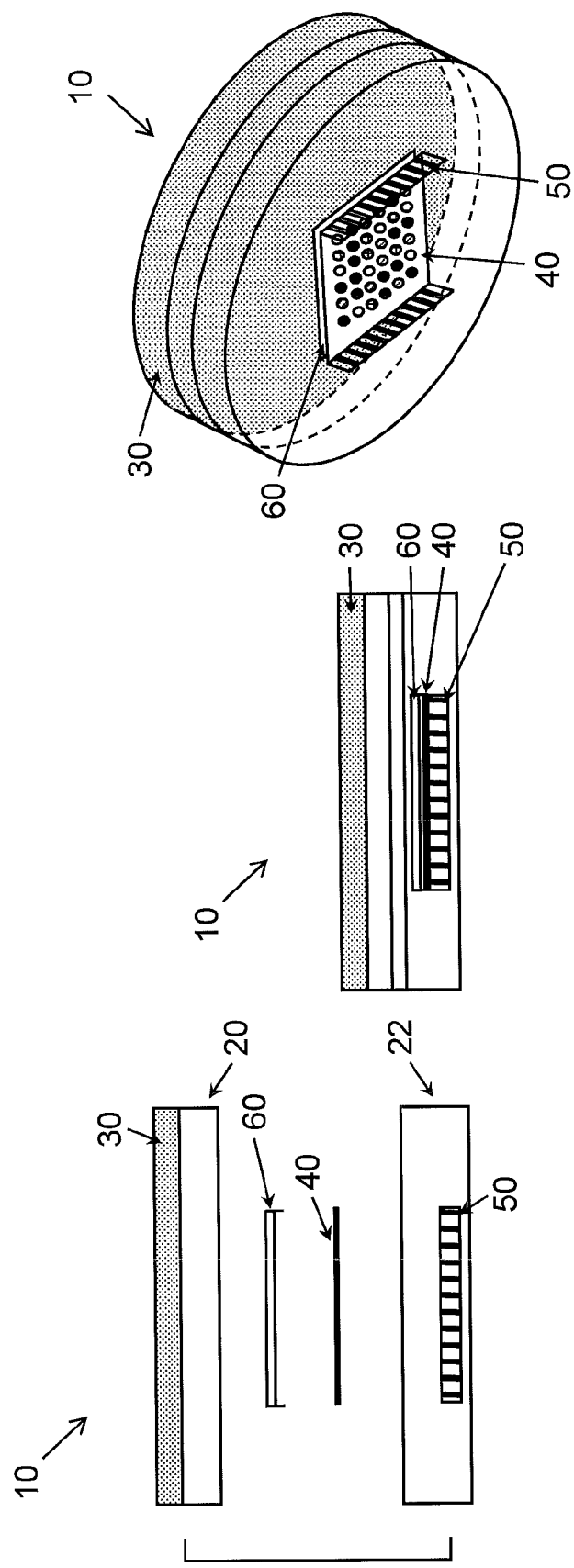

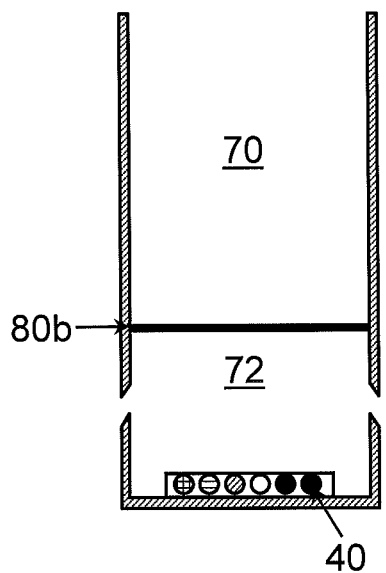
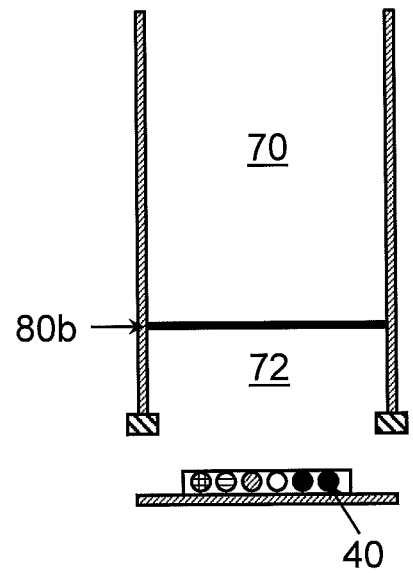
FIG. 2G    FIG. 2H
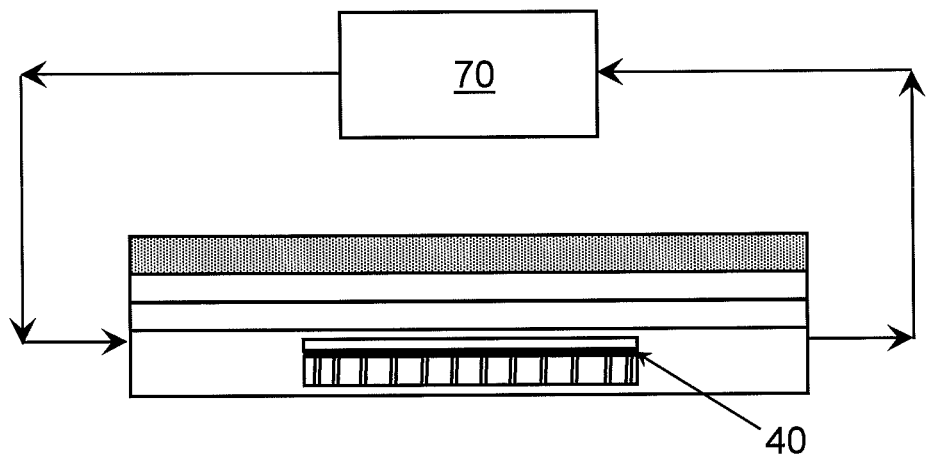
FIG. 3

APPARATUS AND METHOD FOR DETECTING AND IDENTIFYING MICROORGANISMS

INTRODUCTION

This application claims the benefit of U.S. Provisional Application No. 60/829,025 filed Oct. 11, 2006, which is herein incorporated by reference in its entirety.

BACKGROUND OF THE INVENTION

Conventional diagnosis of microbial infections generally relies on cell culturing to detect and identify the microorganism responsible for the infection. While cell culturing is inexpensive, it can be relatively slow because it relies on visual detection of individual bacterial colonies (i.e., ~$10^6$ bacteria). For example, while colonies of a fast growing bacterium can be observed between ~24 to 48 hours, slower growing bacteria require incubation periods of a week or more to detect bacterial colonies. As further alternatives, instruments have been developed using various principles of detection including infrared or fluorescence spectroscopy, bioluminescence, and flow cytometry (Basile, et al. (1998) *Trends Anal. Chem.* 17:95-109; Bird, et al. (1989) *Rapid Salmonella Detection by a Combination of Conductance and Immunological Techniques*; Blackwell Sci. Publications: Oxford, Vol. 25; Fenselau, Ed. (1994) *Mass Spectrometry for the Characterization of Microorganisms* Washington D.C., Vol. 240; Lloyd, Ed. (1993) *Flow Cytometry in Microbiology*; Springer-Verlag London Limited: Germany; Perez, et al. (1998) *Anal. Chem.* 70:2380-2386; Wyatt (1995) *Food Agri. Immunol.* 7:55-65). Among these, the primary physical/chemical methods of bacterial detection are those which involve the detection of some naturally occurring component of the bacterium.

BACT/ALERT uses, for example, a colorimetric sensor detection system which detects microorganism growth by the production of $CO_2$. When the $CO_2$ levels reach a certain level, the sensor turns yellow giving a positive result for bacteria present. This system can be used for a wide variety of microorganisms and has a success rate of 95% in 24 hours and 98% in 72 hours (Weinstein, et al. (1995) *J. Clin. Microbiol.* 33:978-981; Wilson, et al. (1995) *J. Microbiol.* 33:2265-2270; Wilson, et al. (1992) *J. Clin. Microbiol.* 30:323-329).

Other devices and methods for detecting microorganisms are provided in U.S. Pat. Nos. 5,094,955; 6,777,226; 6,197,577; 5,976,827; and 5,912,115. In general, these devices rely on the use of a single sensor (e.g., pH or carbon dioxide indicator) in a layer adjacent to a layer of growth medium for detecting the presence of a bacterium.

Bacterial identification methods usually include a morphological evaluation of microorganisms as well as tests for the organism's ability to grow in various media sources under various conditions. These techniques allow for the detection of single organisms, however, amplification of the signal is required through growth of a single cell into a colony and no single test provides a definitive identification of an unknown bacterium. Traditional methods for the identification of bacteria involve pre-enrichment, selective enrichment, biochemical screening, and serological confirmation (Tietjen & Fung (1995) *Crit. Rev. Microb.* 21:53-83; Kaspar & Tartera (1990) *Methods Microbiol.* 22:497-530; Helrich (1990) *Official Methods of Analysis of Association of Official Analytical Chemists*; 15 ed.; AOAC: Arlington, Va., Vol. 2; Hobson, et al. (1996) *Biosensors & Bioelectronics* 11:455-477).

Alternative methods such as immunoassays and PCR-based approaches have been pursued with varying degrees of success (Iqbal, et al. (2000) *Biosensors & Bioelectronics* 15:549-578; Morse (2000) *Detecting Biological Warfare Agents*; Lynne Rienner Publishers, Inc: Boulder, Colo.). However, in the case of PCR, such an approach is expensive and requires pure samples, hours of processing, and an expertise in microbiology (Spreveslage, et al. (1996) *J. Microbiol. Methods* 26:219-224; Meng, et al. (1996) *Intl. J. Food Microbiol.* 32:103-113). An alternative method, gas chromatography/mass spectrometry (GC/MS), has been used to produce a fatty acid profile or "fingerprint" for the detection and identification of microorganisms (Swaminathan & Feng (1994) *Ann. Rev. Microbiol.* 48:401-426).

Array-based vapor sensing is an approach toward the detection of chemically diverse analytes. Based on cross-responsive sensor elements, rather than specific receptors for specific analytes, these systems produce composite responses unique to an odorant in a fashion similar to the mammalian olfactory system (Stetter & Pensrose, Eds. (2001) *Artificial Chemical Sensing: Olfaction and the Electronic Nose*; Electrochem. Soc.: New Jersey; Gardner & Bartlett (1999) *Electronic Noses: Principles and Applications*; Oxford University Press: New York; Persuad & Dodd (1982) *Nature* 299:352; Albert, et al. (2000) *Chem. Rev.* 100:2595-2626; Lewis (2004) *Acc. Chem. Res.* 37:663-672; James, et al. (2005) *Microchim. Acta* 149:1-17; Walt (2005) *Anal. Chem.* 77:45A). In such arrays, one receptor responds to many analytes and many receptors respond to any given analyte. A distinct pattern of responses produced by the calorimetric sensor array provides a characteristic fingerprint for each analyte. Using such systems, volatile organic compounds have been detected and differentiated (Rakow & Suslick (2000) *Nature* 406:710-713; Suslick & Rakow (2001) *Artificial Chemical Sensing: Olfaction and the Electronic Nose*; Stetter & Penrose, Eds.; Electrochem. Soc.: Pennington, N.J.: pp. 8-14; Suslick, et al. (2004) *Tetrahedron* 60:11133-11138; Suslick (2004) *MRS Bulletin* 29:720-725; Rakow, et al. (2005) *Angew. Chem. Int. Ed.* 44:4528-4532; Zhang & Suslick (2005) *J. Am. Chem. Soc.* 127:11548-11549).

Array technologies of the prior art generally rely on multiple, cross-reactive sensors based primarily on changes in properties (e.g., mass, volume, conductivity) of some set of polymers or on electrochemical oxidations at a set of heated metal oxides. Specific examples include conductive polymers and polymer composites (Gallazzi, et al. (2003) *Sens. Actuators B* 88:178-189; Guadarrana, et al. (2002) *Anal. Chim. Acta* 455:41-47; Garcia-Guzman, et al. (2003) *Sens. Actuators B* 95:232-243; Burl, et al. (2001) *Sens. Actuators B* 72:149-159; Wang, et al. (2003) *Chem. Mater.* 15:375-377; Hopkins & Lewis (2001) *Anal. Chem.* 73:884-892; Feller & Grohens (2004) *Sens. Actuators B* 97:231-242; Ferreira, et al. (2003) *Anal. Chem.* 75:953-955; Riul, et al. (2004) *Sens. Actuators B* 98:77-82; Sotzing, et al. (2000) *Anal. Chem.* 72:3181-3190; Segal, et al. (2005) *Sens. Actuators B* 104: 140-150; Burl, et al. (2002) *Sens. Actuators B* 87:130-149; Severin, et al. (2000) *Anal. Chem.* 72:658-668; Freund & Lewis (1995) *Proc. Natl. Acad. Sci. U.S.A.* 92:2652-2656; Gardner, et al. (1995) *Sens. Actuators B* 26:135-139; Bartlett, et al. (1989) *Sens. Actuators B* 19:125-140; Shurmer, et al. (1990) *Sens. Actuators B* 1:256-260; Lonergan, et al. (1996) *Chem. Mater.* 8:2298-2312), polymers impregnated with a solvatochromic dye or fluorophore (Chen & Chang (2004) *Anal. Chem.* 76:3727-3734; Hsieh & Zellers (2004) *Anal. Chem.* 76:1885-1895; Li, et al. (2003) *Sens. Actuators B* 92:73-80; Albert & Walt (2003) *Anal. Chem.* 75:4161-4167; Epstein, et al. (2002) *Anal. Chem.* 74:1836-1840; Albert, et al. (2001) *Anal. Chem.* 73:2501-2508; Stitzel, et al. (2001) *Anal. Chem.* 73:5266-5271; Albert & Walt (2000) *Anal.*

Chem. 72:1947-1955; Dickinson, et al. (1996) *Nature* 382: 697-700; Dickinson, et al. 1996) *Anal. Chem.* 68:2192-2198; Dickinson, et al. (1999) *Anal. Chem.* 71:2192-2198), mixed metal oxide sensors (Gardner & Bartlett (1992) Sensors and Sensory Systems for an Electronic Nose; Kluwer Academic Publishers: Dordrecht; Zampolli, et al. (2004) *Sens. Actuators B* 101:39-46; Tomchenko, et al. (2003) *Sens. Actuators B* 93:126-134; Nicolas & Romain (2004) *Sens. Actuators B* 99:384-392; Marquis & Vetelino (2001) *Sens. Actuators B* 77:100-110; Ehrmann, et al. (2000) *Sens. Actuators B* 65:247-249; Getino, et al. (1999) *Sens. Actuators B* 59:249-254; Heilig, et al. (1997) *Sens. Actuators B* 43:45-51; Gardner, et al. (1991) *Sens. Actuators B* 4:117-121; Gardner, et al. (1992) *Sens. Actuators B* 6:71-75; Corcoran, et al. (1993) *Sens. Actuator B* 15:32-37; Gardner, et al. (1995) *Sens. Actuators B* 26:135-139), and polymer coated surface acoustic wave (SAW) devices (Grate (2000) *Chem. Rev.* 100:2627-2648; Hsieh & Zellers (2004) *Anal. Chem.* 76:1885-1895; Grate, et al. (2003) *Anal. Chim. Acta* 490:169-184; Penza & Cassano (2003) *Sens. Actuators B* 89:269-284; Levit, et al. (2002) *Sens. Actutors B* 82:241-249; Grate, et al. (2001) *Anal. Chem.* 73:5247-5259; Hierlemann, et al. (2001) *Anal. Chem.* 73:3458-3466; Grate, et al. (2000) *Anal. Chem.* 72:2861-2868; Ballantine, et al. (1986) *Anal. Chem.* 58:3058-3066; Rose-Pehrsson, et al. (1988) *Anal. Chem.* 60:2801-2811; Patrash & Zellers (1993) *Anal. Chem.* 65:2055-2066). However, the sensors disclosed in these prior art references do not provide a diversity of interactions with analytes; interactions are limited to the weakest and least specific of intermolecular interactions, primarily van der Waals and physical adsorption interactions between sensor and analyte. As such, both sensitivity for detection of compounds at low concentrations relative to their vapor pressures and selectivity for discrimination between compounds is compromised with these prior art sensors.

Cross-responsive sensor technologies have also been applied to the identification of bacteria (Lai, et al. (2002) *Laryngoscope* 112:975-979; McEntegart, et al. (2000) *Sensors and Actuators B* 70:170-176; Gibson, et al. (1997) *Sensors and Actuators B* 44:413-422; Ivnitski, et al. (1999) *Biosensors & Bioelectronics* 14:599-624). These cross-responsive sensor technologies have employed a variety of chemical interaction strategies, including the use of conductive polymers (Freund & Lewis (1995) *Proc. Natl. Acad. Sci. USA FIELD Publication Date* 92:2652-2656), conductive polymer/carbon black composites (Lonergan, et al. (1996) *Chem. Mater.* 8:2298-2312), fluorescent dye/polymer systems (Walt (1998) *Acc. Chem. Res.* 31:267-278), tin oxide sensors (Heilig, et al. (1997) *Sensors and Actuators, B: Chemical B*43:45-51), and polymer-coated surface acoustic wave (SAW) devices (Grate (2000) *Chem. Rev.* 100:2627-2647). For example, an array of four metal oxide sensors has been used to detect and identify six pathogenic bacteria by sampling the headspace over the growing microorganisms, wherein the sensor correctly identified/classified 62% of the pathogens (Craven, et al. (1994) *Neural Networks and Expert Systems in Medicine and Healthcare*; University of Plymouth: Plymouth). The use of such technologies for medical application has been described (Thaler, et al. (2001) *Am. J. Rhinology* 15:291-295); however, these systems employ the detection of chemically non-coordinating organic vapors without exploring the detection of the most toxic and odiferous compounds (e.g., phosphines and thiols). In general, most cross-responsive sensor devices of the prior art have limited detection sensitivity and remain quite non-selective (O'Hara (2005) *Clin. Microbiol. Rev.* 18:147-162).

Additional devices for detecting microorganisms are disclosed in U.S. Pat. Nos. 6,030,828; 4,297,173; 4,264,728; 5,795,773; 5,856,175; 6,855,514; 7,183,073; and U.S. Patent Application No. 2005/0170497.

Needed is a cost-efficient, non-invasive, sensitive and selective sensor which can detect, quantify and discriminate between microorganisms. The present invention meets this long-felt need.

SUMMARY OF THE INVENTION

The present invention is an apparatus for detecting and identifying microorganisms. In one embodiment, the apparatus is composed of a medium for supporting growth of a microorganism and at least one calorimetric sensing element placed in or proximate to the medium, wherein said sensing element is composed of an array which has a plurality of chemoresponsive dyes deposited thereon in a predetermined pattern combination, wherein the combination of the dyes have a distinct and direct spectroscopic, transmission, or reflectance response to distinct analytes produced by the microorganism which is indicative of the presence and identity of the microorganism. In accordance with this embodiment, the apparatus further contains an air flow means, or is part of a system which includes a visual imaging means, with some embodiments including an aerating means.

In another embodiment, the apparatus of the invention is composed of a first chamber for culturing a cell, and a second chamber with a sensing element disposed therein, wherein the first chamber and second chamber are separated by a gas impermeable barrier produced from a material selected for being permeabilized. In accordance with this embodiment, the apparatus can further include a medium for supporting growth of a microorganism.

Kits and methods for detecting, quantifying or identifying a microorganism using the apparatus of the invention are also provided.

BRIEF DESCRIPTION OF THE DRAWINGS

FIGS. 1A-1C are illustrations of an apparatus of the invention. FIG. 1A is an exploded side view of the apparatus. FIG. 1B shows a side view of the assembled apparatus. FIG. 1C shows a perspective view of the assembled apparatus with the colorimetric sensing element placed print side down in the bottom of a Petri dish container (i.e., surface of array with chemoresponsive dye is visible from the outside).

FIGS. 2A-2H show illustrations of an apparatus of the invention in the form of a liquid/blood culture bottle. In the embodiment depicted in FIG. 2A, the medium is in the bottom of the bottle and the colorimetric sensing element is in the headspace above the medium. In the embodiment depicted in FIG. 2B, the colorimetric sensing element is placed in the bottom of the bottle and the medium is separated from the colorimetric sensing element by a gas-permeable membrane. In the embodiment depicted in FIG. 2C, the colorimetric sensing element is composed of dyes suspended in a gas-permeable matrix at the bottom of the bottle and the medium is in the main body of the bottle. FIG. 2D depicts embodiments wherein the culture medium is separated from the growth medium by a gas impermeable barrier produced from a material selected for being capable of being permeabilized. FIGS. 2E and 2F depict the apparatus of FIG. 2D, wherein the gas impermeable barrier has been ruptured (FIG. 2E) or made gas permeable (FIG. 2F). FIG. 2G illustrates an overlapping radial seal while FIG. 2H illustrates a capping seal at the bottom of the container.

FIG. 3 depicts a calorimetric sensing element in a petri dish container configured for recirculating flow of headspace. The arrows indicate direction of gas flow.

DETAILED DESCRIPTION OF THE INVENTION

Figure 2A:
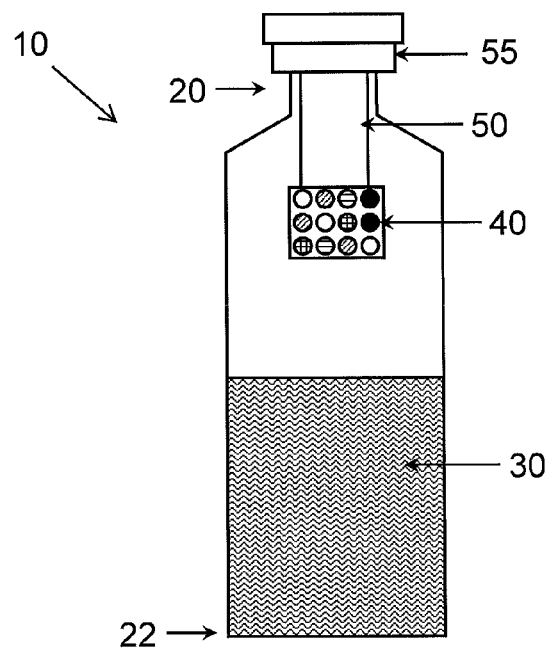

An apparatus and method for using the same are provided which can be advantageously used to detect and identify microorganisms in various applications, including but not limited to disease diagnosis, quality control, and environmental contamination. In particular embodiments, the invention relates the use of chemoresponsive dyes, such as Lewis acid/base dyes (e.g., metalloporphyrin), Brnsted acidic or basic dyes (e.g., pH indicators) and dyes with large permanent dipoles (e.g., zwitterionic solvatochromic dyes), for detecting and identifying microorganisms based upon analytes produced by the microorganisms.

As depicted in FIG. 1, the instant apparatus 10 is a container in the form of, e.g., a petri dish, with at least one interior side 20 (e.g., the top side) containing a medium 30 for supporting growth of at least one microorganism in a sample, and the opposite interior side 22 (e.g., the bottom side) having affixed thereto a sensing element 40, which when in use is placed in or proximate to medium 30. In particular embodiments, the sensing element is not in contact with the surface of the medium.

Additional features of the instant apparatus can include a support means 50 and retaining means 60 (FIG. 1) for positioning sensing element 40 in the headspace of microorganisms growing on or in medium 30. It is contemplated that the bottom 22 of the interior side of apparatus 10 can be modified to provide support means 50 for holding sensing element 40. Support means 50 can be integral with apparatus 10, wherein in use sensing element 40 is placed on support means 50 and retainer means 60 holds sensing element 40 in place on support means 50 and prevents it from moving. Retainer means 60 can snap in place, be chemically or ultrasonically welded in place, glued in place, etc. While some embodiments embrace a removable sensing element 40, other embodiments provide that sensing element 40 is permanently fixed to support means 50, thereby obviating the need of retainer means 60.

Figure 2B:
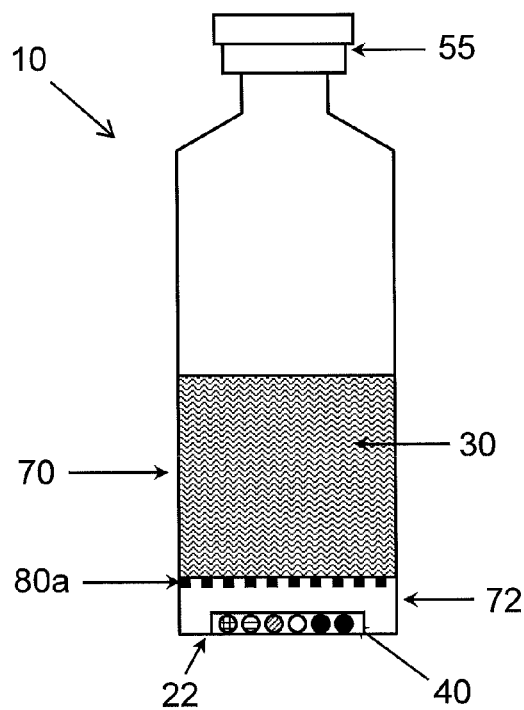
Figure 2C:
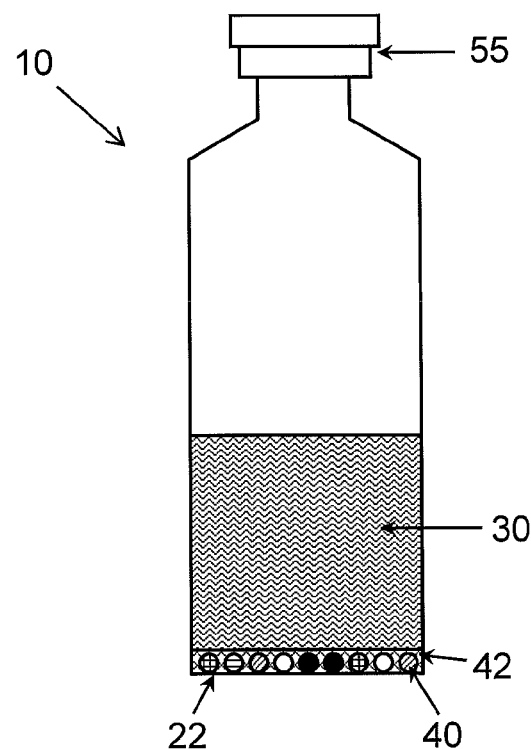

For the purpose of disclosing the instant apparatus, the terms "top" and "bottom" are used herein to describe two opposing sides and are not to be construed as limiting the instant apparatus to any particular orientation or configuration. In this regard, other configurations such as bottles or vials are also embraced by the present invention. By way of illustration, the configuration depicted in FIG. 2A shows the instant apparatus in the form of a bottle, wherein medium 30 (e.g., a blood culture medium) is in the bottom 22 of apparatus 10 with sensing element 40 positioned at the top 20 of apparatus 10 via support means 50 attached to a cap or lid 55. In the bottle configuration depicted in FIG. 2B, medium 30 is in a first chamber 70 of apparatus 10 with sensing element 40 located in a second chamber 72 (and optionally affixed to the bottom 22 of apparatus 10), wherein the first chamber 70 and second chamber 72 are separated by a gas-permeable barrier 80a. Alternatively, the embodiment shown in FIG. 2C provides for the direct application of sensing element 40 to the bottom 22 of apparatus 10 in the form of sensing dyes suspended in gas-permeable matrix 42. Thus, while sensing element 40 depicted in FIG. 2A can be monitored from the side of apparatus 10, sensing element 40 depicted in FIGS. 2B and 2C can be monitored from the bottom 22 of apparatus 10.

Figure 2D:
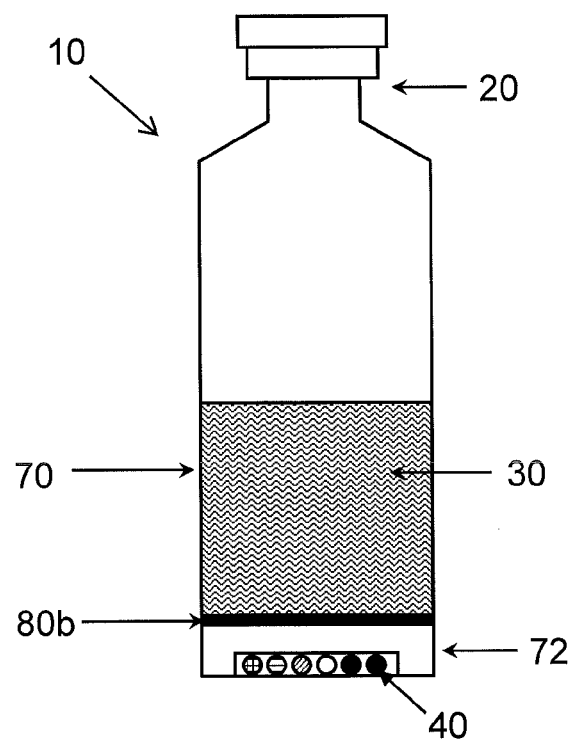
Figure 2E:
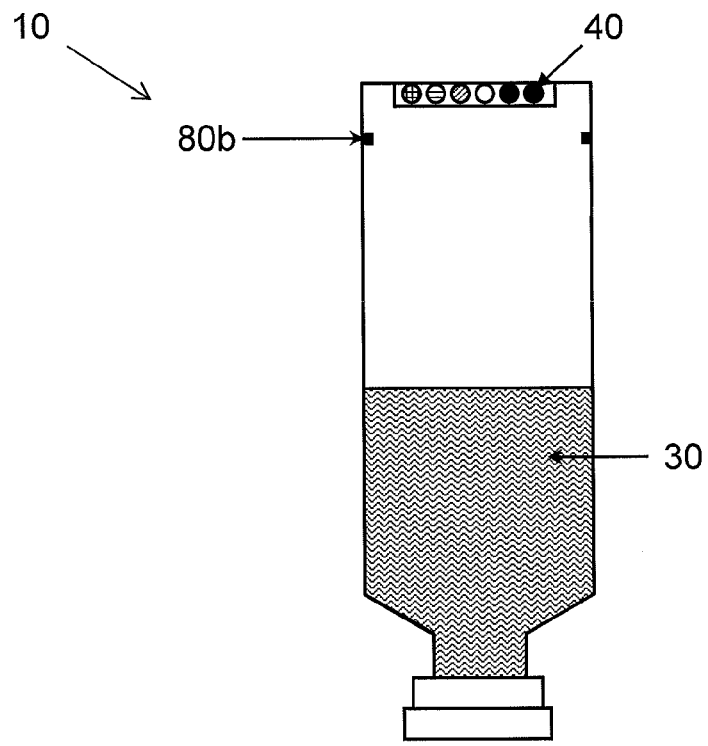
Figure 2F:
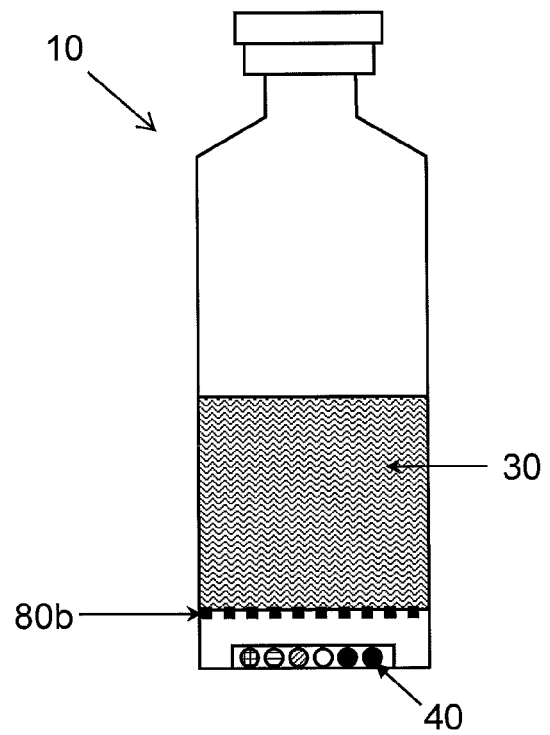

In yet another embodiment of the invention, a dual-chamber apparatus 10 is provided, wherein the chambers are separated by a gas impermeable barrier. As illustrated in FIG. 2D, the first chamber 70 of apparatus 10 holds media 30, whereas the second chamber 72 contains the sensing element 40 interfaced to a transparent area such that the sensing element 40 can be viewed from outside apparatus 10. First chamber 70 and second chamber 72 are separated by gas impermeable barrier 80b so that sensing element 40 is not exposed to media 30 or other components within the first chamber 70 until a user-designated time point. At that point, the baseline value of the sensing element 40 can be measured (e.g., color, pressure, fluorescence or other signal), barrier 80b can be ruptured or otherwise made permeable, and changes in sensor element 40 characteristics can be monitored, e.g., at regular time points thereafter. In accordance with this configuration of the instant apparatus, gas impermeable barrier 80b can be permeabilized by rupturing or breaking barrier 80b (e.g., via mechanical puncturing using a device equivalent to a needle or nail that is inserted through the top 20 of apparatus 10) to expose sensing element 40 to the media 30 or headspace above the media. In this regard, FIG. 2E depicts the inversion of apparatus 10 so that sensing element 40 is in the headspace above medium 30 after permeabilization of gas impermeable barrier 80b. Alternatively, gas impermeable barrier 80b can be permeabilized to gases (and therefore structurally intact) at a user-designated time point and the container maintained in an upright posture (see FIG. 2F). For example, it is contemplated that gas permeability of a gas impermeable barrier 80b can be modified by exposure to ultrasound; applied electric field; a change in temperature, pH, humidity, etc. By way of illustration, Ito, et al. ((1997) *Die Angewadndte Makromolekulare Chemie* 248:85-94), teach that chitosan membrane has a low permeability for gases in its dry state; however, permeability to gases such as carbon dioxide increases upon exposure to water vapor. Similarly, Kulshrestha, et al. ((2005) *Bull. Mater. Sci.* 28:643-646) teach that the permeability of polyethersulphone membranes to $H_2$ and $CO_2$ increased with increasing temperature.

As can be appreciated by the skilled artisan, the configuration shown in FIG. 1 may be more suitable for solid or certain semi-solid media whereas the configurations shown in FIG. 2 may be more suitable for liquid or semi-liquid media.

In some embodiments, all or a portion of the container is transparent or translucent such that changes in the sensing element 40 can be detected. In particular embodiments, the portion of apparatus 10 containing sensing element 40 is preferably transparent for viewing/imaging changes in sensing element 40 due to microorganism growth and production of analytes.

Though the apparatus can be open such that the interior air is exchanged with the exterior air, it is desirable that the apparatus be a sealed or sealable container. The container may be sealed by snapping or screwing the top and bottom sides together or by using a permeable or semi-permeable sealing film (e.g., PARAFILM) or any combination thereof (or any other sealing device). Alternatively, a plug or stopper can be employed, e.g., in configurations employing bottle-shaped containers. The container itself can be composed of either a gas-permeable or a gas-impermeable material, depending on the growth requirements of the microorganism. Different container composition materials can include laminates (gas impermeable and/or hydrophobic gas-permeable membranes) or other suitable materials well-known in the art (e.g., glass) for producing culture plates, vials or bottles. Moreover, the container can be modified with vents (e.g., a gas permeable membrane in an opening of the container wall).

In accordance with embodiments pertaining to a dual-chambered apparatus, it is contemplated that apparatus 10 can be produced by an overlapping radial seal (see FIG. 2G) or by employing a capping seal at the bottom of the apparatus 10 (FIG. 2H) to generate the second chamber 72 housing sensing element 40.

As illustrated in FIG. 1, FIG. 2A and FIG. 2E, sensing element 40 is positioned in the headspace above medium 30 in such a manner that the volatile analytes generated by the microorganisms reach sensing element 40 by simple diffusion. However, an alternative embodiment shown in FIG. 3 provides an integrated, recirculating gas (air) pump 70 to establish a dynamic flow of headspace across sensing element 40 such that the response time of the sensing element 40 to the analytes can be reduced.

Figures 4A, 4B:
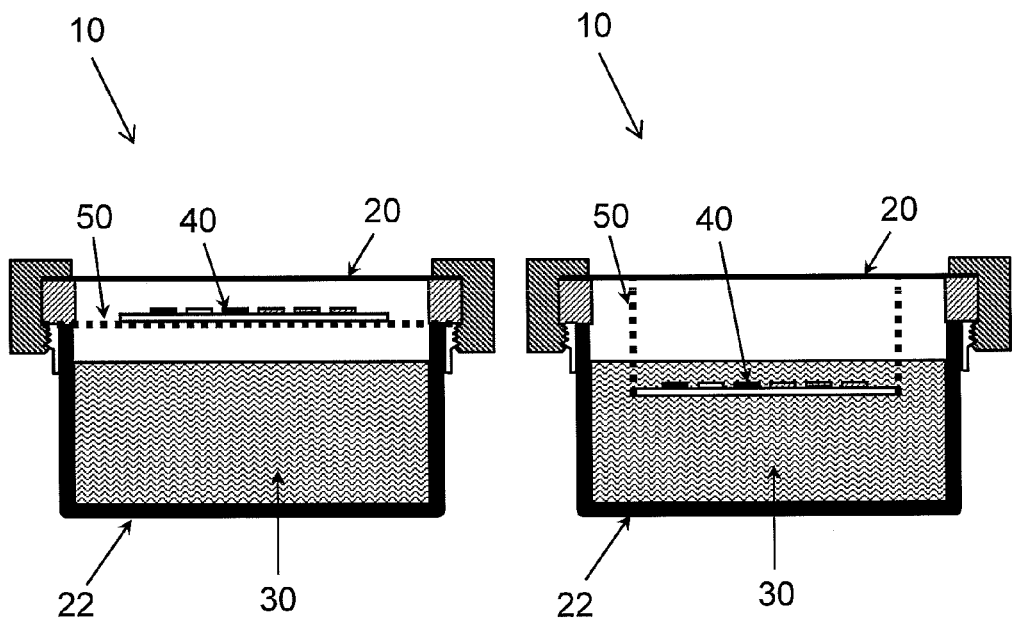
FIGS. 4A-4B show an apparatus of the invention employing a liquid or semi-liquid medium, wherein the colorimetric sensing element is positioned proximate to the medium (FIG. 4A) as compared to being placed in the medium (FIG. 4B).

Furthermore, some embodiments embrace sensing element 40 positioned in the headspace (see, e.g., FIGS. 2A, 2E and 4A), while other embodiments embrace a colorimetric sensing element in contact with or placed in the medium. By way of illustration, FIG. 4B shows medium 30 in the bottom 22 of apparatus 10 with colorimetric sensing element 40 affixed via support means 50 to the top 20 of apparatus 10 and positioned in medium 30 when in use.

As the skilled artisan can appreciate, a variety of different media can be employed in the instant invention. The growth medium of the instant apparatus can be a solid, semi-solid, or liquid formulation that contains nutrients for supporting growth of one or more microorganisms. As used herein, a solid medium is defined as any formulation that holds its own form or shape, at least for a few minutes, and hence includes gelatin growth medium. In one embodiment, the growth medium is preformed and the sample subsequently applied to the medium. For example, a liquid sample could be applied onto an already gelled medium or onto a dehydrated or partially dehydrated gel medium so as to immobilize the microorganisms on the surface of the medium. Alternatively, the sample itself can be a liquid, semi-solid or semi-liquid (e.g., paste or gel) and used in the preparation of the medium or a layer of the medium. For example, a liquid sample can be mixed with a dry powdered gelling agent to form a solid or semi-solid matrix which is applied to the surface of a preformed growth medium before gelling has occurred. As a further alternative, the sample is applied to the surface of the growth medium on a non-gel absorbent material, such as a sponge material, cellulose, glass fiber, filter paper, etc.

Semi-solid or solid media can be prepared using any suitable gelling agent or combination of gelling agents including natural and synthetic hydrogel powders, gums, agars, agaroses, carageenans, bentonite, alginates, collagens, gelatins, fused silicates, water soluble starches, polyacrylates, celluloses, cellulose derivatives, polyethylene glycols, polyethylene oxides, polyvinyl alcohols, dextrans, polyacrylamides, polysaccharides or any other gelling or viscosity enhancing agents.

The nutritional components that make up a complex microbial medium influence the metabolic pathways used by microorganisms. Organic acids, bases and various analytes are produced in proportions dependent on the nutrients available. These metabolic products also vary from species to species of microorganism and can advantageously be detected and used in the identification of one or more microorganisms in a sample. The amount of metabolites produced by microorganisms increases with increased growth time and increased initial concentration. The amount of microorganism present depends on the type of microorganism, its growth rate, the medium, and the growth environment. The type and amount of metabolites produced by microorganisms depend on all of the above factors as well as the growth phase of the microorganism. Accordingly, the medium of the instant invention is added to provide nutrients for the growth of microorganisms so that colorimetric sensing element-detectable analytes are produced. Many types of media are well-known in the art for different types of microorganisms. For example, for supporting the growth of an aerobic organism, the media can include, e.g., tryptone, soytone, proteose peptone, malt extract, dextrose and MOPS. If the microorganism is an anaerobic organism, the media can further include the media listed above for aerobic organisms, as well as Hemin, L-cystine and Menadione. For coliforms, the media can include, e.g., Lactose, bile salts #3, $K_2HPO_4$, $KH_2PO_4$, $(NH_4)_2SO_4$, $MgSO_4$, Na-bisulfide and SDS. For yeast, mold and other acid tolerant microorganisms, the media can include, e.g., dextrose, yeast extract, $(NH_4)$ citrate and tartaric acid to a pH of 5.5. Liquid culture media, including blood culture media, is also encompassed within the scope of the invention.

The medium can also contain conditioning components, such as lytic agents, lytic enzymes, antibiotic neutralizers, surfactants or other materials helpful for improving microorganism detection capabilities. Alternatively, conditioning components can be combined with the sample or in a separate layer of medium.

Lytic agents for conditioning can be added for lysing blood cells in the sample, for allowing for a smoother gel, and/or for better rehydration of the gel. Examples of possible lytic agents include saponin, digitonin, TWEEN, polysorbitan monolaurate, and other surfactants. Lytic enzymes, typically though not necessarily proteolytic enzymes, can be added for digesting cellular material in a blood sample, for making a smoother gel, and/or for better rehydration of the gel. The lytic enzymes for conditioning can include one or more proteases, for example an enzyme mixture derived from *Aspergillus oryzae*, or the like.

Antibiotic neutralizers can be added for conditioning, in particular for faster and/or better recovery of microorganisms in the sample. One or more of such neutralizers could be selected from resins, gums, and carbon-based materials (e.g., activated charcoal or ECOSORB), or one of a variety of enzymes to specifically degrade various antibiotics (e.g., beta lactamase).

A variety of different sensor types can also be used in this invention. While some embodiments embrace the use of conventional pressure, pH, or temperature sensing elements, particular embodiments of the present invention embrace the detection of at least one analyte via a sensing element composed of an array of chemoresponsive dye spots that change color upon contact with various gases or vapors, i.e., a calorimetric sensing element. In this regard, the sensing element can be preselected to sense one analyte or alternatively sense a plurality of analytes.

A calorimetric sensing element of the present invention is a substrate with a plurality of chemoresponsive dyes deposited thereon in a predetermined pattern combination. The substrate for retaining the chemoresponsive dyes can be the apparatus itself or be composed of any suitable material or materials, including but not limited to, chromatography plates, paper, filter papers, porous membranes, or properly machined polymers, glasses, or metals. However, particular embodiments embrace the use of a hydrophobic substrate. Dyes can be covalently or non-covalently affixed in or on a calorimetric sensing element substrate by direct deposition, including, but not limited to, airbrushing, ink-jet printing, screen printing, stamping, micropipette spotting, or nanoliter dispensing. In embodiments drawn to the apparatus itself for use a substrate, the chemoresponsive dye can be dispersed in a liquid polymer solution, similar to silicon caulking prior to curing. Individual polymer-dye solutions are then placed onto the surface of the apparatus to form an array of chemoresponsive dyes on the surface of the apparatus. See, for example FIG. 2C.

When the sensing element is provided on a substrate which is not the apparatus itself, the sensing element is preferably affixed (e.g., by an adhesive or retaining means) inside a transparent portion of the apparatus so that it is visible from the outside of the apparatus. It is contemplated that the sensing element can also be placed outside the apparatus, as long as a method is provided that allows the metabolic changes due to the microorganisms to affect the sensor.

In the illustrative embodiments disclosed in FIGS. 1, 2 and 4, sensing element 40 is positioned in apparatus 10 with the printed dye surface facing to the outside. Sensing element 40 is exposed to analytes in medium 30 (FIG. 4B) or to analytes present in the headspace above medium 30 via support means 50, which can be vented to allow analytes produced by the microorganisms to flow over sensing element 40 (see FIGS. 1, 2A, 2E and 4A). As such, sensing element 40 may or may not be flush against the inside surface of the apparatus. In embodiments wherein medium 30 is in the background of sensing element 40 when sensing element 40 is being viewed from the outside of container 20, it is desirable that the sensing element substrate is opaque. By "opaque", it is meant that the substrate sufficiently blocks the viewing or detecting (in any relevant electromagnetic region) of the sample and/or actual microorganism colonies in or on the medium from the opposite side of the sensing element (e.g., semi-opaque, substantially opaque, or fully opaque). Though it is possible to have a transparent or relatively transparent colorimetric sensing element substrate if the sample is also substantially transparent, it is generally desired that the calorimetric sensing element substrate not be transparent.

Figure 5:
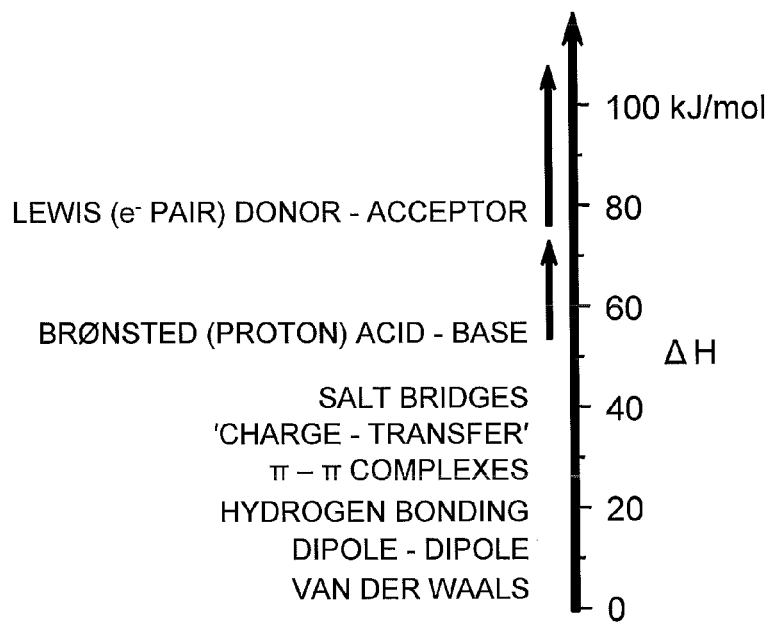
FIG. 5 depicts intermolecular interactions on a semi-quantitative energy scale.

In general, the detection and identification of compounds using a colorimetric sensing element is fundamentally based upon supramolecular chemistry and intrinsically relies on the interactions between molecules, atoms, and ions. The classification of inter-molecular interactions is well-established (FIG. 5) and involves bond formation and coordination, acid-base interactions, hydrogen-bonding, charge-transfer and pi-pi molecular complexation, dipolar and multipolar interactions, as well as weak interactions such as van der Waals interaction and physical adsorption. In contrast to the prior art, the instant invention advantageously employs chemoresponsive dyes have strong interactions, e.g., greater than 10 kJ/mol or preferably greater than 25 kJ/mol, with analytes produced by microorganisms.

To achieve such strong interactions and further provide a means for detection, the chemically responsive or chemoresponsive dyes employed in the instant calorimetric sensing element each contain a center to interact strongly with analytes, and each interaction center is strongly coupled to an intense chromophore. As used herein, chemoresponsive dyes are dyes that change color, in either reflected or absorbed light, upon changes in their chemical environment.

Chemoresponsive dye classes which provide the desired interactions and chromophores include Lewis acid/base dyes (i.e., metal ion containing dyes), Brnsted acidic or basic dyes (i.e., pH indicators), and dyes with large permanent dipoles (i.e., zwitterionic solvatochromic dyes). The importance of strong sensor-analyte interactions is highlighted by indications that the mammalian olfactory receptors are, in many cases, metalloproteins and that odorant ligation to the metal center is intrinsic to the mechanism of action (Wang, et al. (2003) *Proc. Natl. Acad. Sci. U.S.A.* 100:3035-3039).

To detect and distinguish a multitude of analytes, the instant apparatus can employ a plurality of chemoresponsive dyes. In accordance with the present invention, the plurality of dyes is deposited on the array substrate in a predetermined pattern combination. Alternatively stated, the dyes are arranged in a two-dimensional spatially-resolved configuration so that upon interaction with one or more analytes, a distinct color and intensity response of each dye creates a signature indicative of the one or more analytes. A plurality of chemoresponsive dyes encompasses 2, 3, 4, 5, 6, 7, 8, 9, 10, 15, 20, 25, 30, 35, 40, or 50 individual dyes. In particular embodiments, a plurality of chemoresponsive dyes is 2 or more, 5 or more, 10 or more, 15 or more, 20 or more, 25 or more, or 30 or more dyes. The chemoresponsive dyes can be deposited in predetermined pattern combinations of rows, columns, spirals, etc., and one or more chemoresponsive dye arrays can be used in a container.

For recognition of analytes with Lewis acid/base capabilities, the use of porphyrins and their metal complexes is desirable. Metalloporphyrins are ideal for the detection of metal-ligating vapors because of their open coordination sites for axial ligation, their large spectroscopic shifts upon ligand binding, their intense coloration, and their ability to provide ligand differentiation based on metal-selective coordination. Furthermore, metalloporphyrins are cross-responsive dyes, showing responses to a large variety of different analytes to different degrees and by different color changes.

A Lewis acid/base dye is defined as a dye which has been identified for its ability to interact with analytes by acceptor-donor sharing of a pair of electrons from the analyte. This results in a change in color and/or intensity of color that indicates the presence of the analyte.

Lewis acid/base dyes include metal ion-containing or three-coordinate boron-containing dyes. Exemplary Lewis acids include, but are not limited to, metal ion-containing porphyrins (i.e., metalloporphyrins), salen complexes, chlorins, bispocket porphyrins, and phthalocyanines. Particularly suitable metal ions complexed with dyes for detecting ammonia include Zn(II) and Co(III) metals. In particular embodiments of the present invention, the Lewis acid dye is a metalloporphyrin. For example, diversity within the metalloporphyrins can be obtained by variation of the parent porphyrin, the porphyrin metal center, or the peripheral porphyrin substituents. The parent porphyrin is also referred to as a free base porphyrin, which has two central nitrogen atoms protonated (i.e., hydrogen cations bonded to two of the central pyrrole nitrogen atoms). A particularly suitable parent porphyrin is 5,10,15,20-tetraphenylporphyrinate(−2) (TPP dianion), its metalated complexes, its so-called free base form ($H_2TPP$) and its acid forms ($H_3TPP^+$ and $H_4TPP^{+2}$). Suitable metal ion-containing metalloporphyrin dyes for use in the apparatus and method of the present invention include, but are not limited to, 2,3,7,8,12,13,17,18-octafluoro-5,10,15,20-tetrakis-(pentafluorophenyl)porphyrinatocobalt(II) [$Co(F_{28}TPP)$];

2,3,7,8,12,13,17,18-octabromo-5,10,15,20-tetraphenylporphyrinatozinc(II) [$Zn(Br_8TPP)$];

5,10,15,20-tetraphenylporphyrinatozinc(II) [ZnTPP];

5(phenyl)-10,15,20-trikis(2',6'-bis(dimethyl-t-butylsiloxyl)phenyl) porphyrinatozinc(II) [$Zn(Si_6PP)$];

5,10,15,20-tetrakis(2',6'-bis(dimethyl-t-butylsiloxyl)phenyl)porphyrinatozinc(II) [$Zn(Si_8PP)$];

5,10,15,20-Tetraphenyl-porphyrinatocobalt (II) [CoTPP];

5,10,15,20-Tetrakis(2,6-difluorophenyl)porphyrinatozinc (II) [Zn-F2PP]; and 5,10,15,20-Tetrakis(2,4,6-trimethylphenyl)porphyrinatozinc(II) [ZnTMP].

The synthesis of such porphyrins is well-established in the art and is described in U.S. patent application Ser. No. 10/279,788.

A Brnsted acid dye of the present invention is a pH indicator dye which changes color in response to changes in the proton (Brnsted) acidity or basicity of the environment. For example, Brnsted acid dyes are, in general, non-metalated dyes that are proton donors which can change color by donating a proton to a Brnsted base (i.e., a proton acceptor). Brnsted acid dyes include, but are not limited to, protonated, but non-metalated, porphyrins, chlorins, bispocket porphyrins, phthalocyanines, and related polypyrrolic dyes. Polypyrrolic dyes, when protonated, are in general pH-sensitive dyes (i.e., pH indicator or acid-base indicator dyes that change color upon exposure to acids or bases)

In one embodiment, a Brnsted acid dye is a non-metalated porphyrin such as 5,10,15,20-tetrakis(2',6'-bis(dimethyl-t-butylsiloxyl)phenyl)porphyrin dication [$H_4Si_8PP$]$^{+2}$; 5,10, 15,20-Tetraphenyl-21H,23H-porphine [$H_2TPP$]; or 5,10,15, 20-Tetraphenylporphine dication [$H_4TPP$]$^{+2}$. In another embodiment of the instant invention, a selected Brnsted dye is an indicator dye including, but not limited to, Bromocresol Purple, Cresol Red, Congo Red, Thymol Blue, Bromocresol Green, Nile Red, Bromothymol Blue, Methyl Red, Nitrazine Yellow, Phenol Red, Bromophenol Red, Disperse Orange 25, and Bromophenol Blue. As will be appreciated by the skilled artisan, the Brnsted acids disclosed herein may also be considered Brnsted bases under particular pH conditions. Likewise, a non-metalated, non-protonated, free base form of a bispocket porphyrin may also be considered a Brnsted base. However, these dye forms are also expressly considered to be within the scope of the dyes disclosed herein.

Solvatochromic dyes change color in response to changes in the general polarity of their environment, primarily through strong dipole-dipole and dispersion interactions. To some extent, all dyes inherently are solvatochromic, with some being more responsive than others. Particular examples of suitable solvatochromic dyes include, but are not limited to Reichardt's dyes, 4-hydroxystyryl-pyridinium dye, 4-methoxycarbonyl-1-ethylpyridinium iodide, and 2,6-diphenyl-4-(2,4,6-triphenyl-1-pyridinio)-phenolate.

The addition of at least one Brnsted acid dye to an array containing at least one metal ion-containing Lewis acid dye can improve the sensitivity of the array for particular analytes and increase the ability to discriminate between analytes. For example, a calorimetric sensing element similar to that of the present invention has been shown to detect volatile organic compounds and complex mixtures down to ppb levels (Rakow, et al. (2005) *Angew. Chem. Int. Ed.* 44:4528-4532). Further, the use of one or more metal ion-containing dyes in combination with one or more Brnsted acid dyes can advantageously create a signature indicative of the presence of a particular analyte. Thus, while some embodiments embrace the use of at least one Lewis acid and/or base dye, one Brnsted acidic and/or basic dye, or one zwitterionic solvatochromic dye, other embodiments of this invention embrace the use at least two different classes of dyes on the instant arrays. In one embodiment, the calorimetric sensing element contains at least one Lewis acid and/or base dye, one Brnsted acidic and/or basic dye, or one zwitterionic solvatochromic dye. In another embodiment, the calorimetric sensing element contains at least one Lewis acid and/or base dye and one Brnsted acidic and/or basic dye. In a further embodiment, the colorimetric sensing element contains at least one Lewis acid and/or base dye and one zwitterionic solvatochromic dye. In yet a further embodiment, the calorimetric sensing element contains at least one Brnsted acidic and/or basic dye and one zwitterionic solvatochromic dye. Still further embodiments embrace the use at least three different classes of dyes on the instant arrays, i.e., at least one Lewis acid and/or base dye, one Brnsted acidic and/or basic dye, and one zwitterionic solvatochromic dye.

The interference of atmospheric humidity on sensor performance is a problem with cross-responsive sensors of the prior art. The high concentration of water vapor in the environment and its large and changeable range makes the accurate detection of analytes at low concentration difficult with the prior art sensors. Water vapor ranges in the environment from <2000 to >20,000 ppmv. Thus, when detecting a few ppmv of an analyte, or even a few ppb, even a very low level of interference from water is intolerable. Physisorption of molecules on surfaces is dominated by the relative hydrophobicity of the adsorbate and adsorbent. Therefore, a disadvantage of the cross-responsive sensor technology of the prior art is sensitivity to changes in humidity.

In contrast, the dyes of the instant calorimetric sensing element are selected from hydrophobic, water-insoluble dyes which are contact-printed as non-aqueous, hydrophobic solutions onto hydrophobic substrates. As such, the instant colorimetric sensing element is essentially impervious to changes in relative humidity (RH). For example, a colorimetric sensing element exposed to water vapor from pure water (RH 100%) or to saturated salt solutions whose water vapor pressures ranged from 11% to 94% RH shows that the dyes in the colorimetric sensing element are unresponsive to water vapor. Similarly, the response to other analytes is not affected by the presence or absence of RH over this range. As such, particular embodiments of the instant colorimetric sensing elements can be used directly in water for the sensing of dilute aqueous solutions of organic compounds (Zhang & Suslick (2005) supra). Therefore, in particular embodiments, chemoresponsive dyes of the instant invention are hydrophobic or water-insoluble. As used herein hydrophobic is used in the conventional sense to describe a compound which is incapable of dissolving in water.

Advantageously, the instant calorimetric sensing element probes the full range of intermolecular interactions to facilitate the detection of analytes such as amines, phosphines, thiols, alcohol, etc., produced by microorganisms. By way of illustration Table 1 provides a list of dyes, the analytes which the dyes can detect, and the resulting color change. Further, the sensing element of the invention is sensitive and robust (i.e., stable to exposure to analytes or the environment). Desirably, this is achieved by employing disposable sensors, which are not integrated to the readout device, thus unlinking the opposing demands of the sensor.

TABLE 1

| Dye | Analyte | Color Change |
| --- | --- | --- |
| Cresol Red (basic) | Carbon dioxide | Violet –> Yellow |
| Phenol Red (basic) | Carbon dioxide | Red –> Yellow |
| Bromocresol Green | Ammonia | Yellow –> Green Yellow –> Blue |
| Reichardt's Dye | Acetic Acid | Blue –> Colorless |
| Tetraphenylporphirinato manganese (III) chloride [MnTPPCl] | Ethanol | Green –> Brown |
| Tetraphenylporphirinato cobalt (III) chloride [CoTPPCl] | Pyridine | Red –> Green |
| Zinc tetraphenylorphyrin [ZnTPP] | Methyl amine | Maroon –> Brown |
| Tetraphenylporphyrin [$H_2$TPP] | Hydrogen chloride | Brown –> Green |
| Tetraphenylporphyrin [$H_4^{+2}$TPP] (diprotonated) | Ammonia | Green –> Brown |
| Bismuth(III) neodecanoate | Hydrogen Sulfide | Colorless –> Black |
| Tetra(2,6-dihydroxy)phenyl porphyrin(with $HgBr_2$) | Hydrogen Cyanide | Brown –> Green |
| Copper(II) acetylacetonate | Hydrogen Sulfide | Sky blue –> Brown |
| Copper(II) acetylacetonate | Methanethiol | Sky blue –> Brown |
| Palladium(II) acetate | Methanethiol | Light yellow –> Dark Yellow |
| Palladium(II) acetate | Hydrogen Sulfide | Light yellow –> Brown |
| Zinc tetramesitylporphyrin (ZnTMP) | Chlorine | Deep pink –> Green |
| Thymol Blue | Triethyl amine | Maroon –> Brown |
| Zinc Tetra(2,6-difluorophenyl)porphyrin | Alcohol | Pink –> Sandy brown |

The present invention is an improvement over the "optoelectronic nose" which is based on the colorimetric array detection using a chemically diverse range of chemically responsive dyes (Rakow & Suslick (2000) supra; Suslick & Rakow (2001) supra; Suslick, et al. (2004) supra; Suslick (2004) supra; Rakow, et al. (2005) supra; Zhang & Suslick (2005) supra; U.S. Pat. Nos. 6,368,558 and 6,495,102). In the instant invention, olfactory-like responses are converted to a visual output which can be readily detected and analyzed by digital imaging and pattern recognition techniques (Beebe, et al. (1998) *Chemometrics: Practical Guide*; J. Wiley & Sons, Inc.: New York; Haswell, Ed. (1992) *Practical Guide to Chemometrics*; Marcel Dekker, Inc.: New York).

In this regard, the apparatus of the instant invention can further be combined with a visual imaging means for monitoring changes of the sensing element. In embodiments pertaining to a colorimetric sensing element, the visual imaging means monitors the spectroscopic response, transmission response or reflectance response of the dyes on the colorimetric sensing element at one or more wavelengths in a spatially resolved fashion so that all of the spots in the colorimetric sensing element are individually imaged or addressed and the color of each spot is individually determined. For the purposes of the present invention, the terms color and calorimetric are intended to include wavelengths in the visible portion of the electromagnetic spectrum, as well as the invisible portion of the electromagnetic spectrum, e.g., infrared and ultraviolet. Color detection can be accomplished with an imaging spectrophotometer, a flatbed scanner, slide scanner, a video or CCD or CMOS digital camera, or a light source combined with a CCD or CMOS detector. Any still or video as well as analog or digital camera can be employed. Moreover, any imaging format can be used, e.g., RGB (red, green and blue) or YUV. Even the simple gray scale imaging can be used. When used in combination with calorimetric sensing elements and image analysis software, calorimetric differences can be generated by subtracting the RGB values of dye images generated before and after exposure of the dye to a sample. The colorimetric differences represent hue and intensity profiles for the array in response to analytes produced by microorganisms. This eliminates the need for extensive and expensive signal transduction hardware associated with previous techniques (e.g., piezoelectric or semiconductor sensors). When used in accordance with the method of the present invention, a unique color change signature can be created which provides both qualitative recognition and quantitative analysis of microorganisms present in a sample.

The sensitivity of the instant calorimetric sensing element is primarily a function of two factors, the ability of a dye spot to change color when exposed to an analyte and the ability of the imaging system to detect that color change. An optical spectroscopic measurement system can divide the visible spectrum into as many as 500 individual bandpass windows whereas a three-color imaging system by definition contains only three such windows. An optical spectroscopic measurement system is therefore capable of detecting smaller color changes than can be detected by three-color imaging systems, effectively increasing the sensitivity of the entire cross-responsive sensing system. Accordingly, in particular embodiments of the present invention, an optical spectroscopic measurement system is employed as a visual imaging means. As used herein, optical spectroscopic measurement systems refer to any system that yields higher color resolution than a three-color imaging system. This can be an imaging spectrograph, fiber optic probe(s) coupled to a spectrograph, or other spectroscopic system.

Figure 6A:
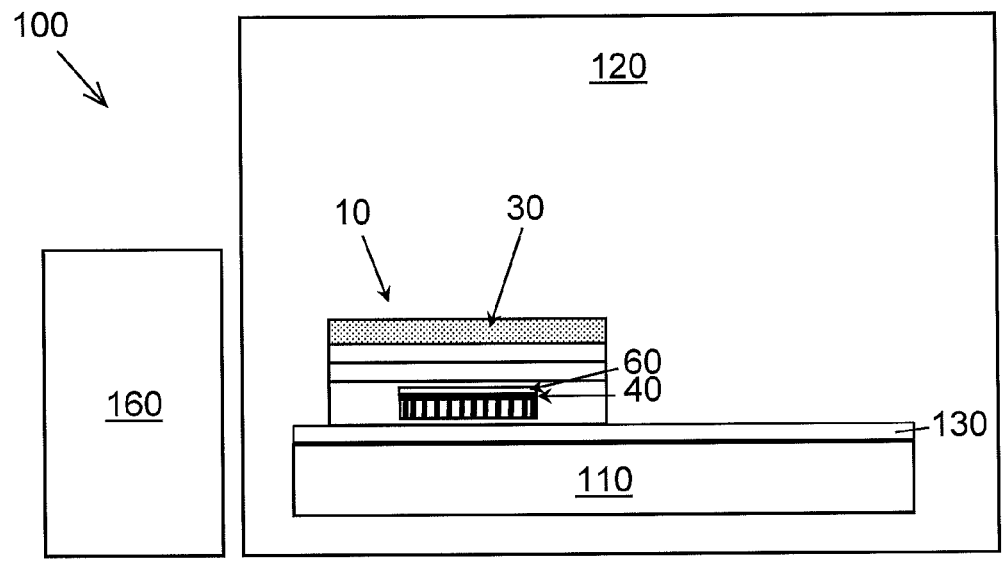
FIGS. 6A-6B show an integrated system for detecting and identifying microorganisms, wherein the apparatus is placed in a growth chamber equipped with an imaging system. Image and data analysis are performed by a computer. The integrated system can be stationary (FIG. 6A) or provide an aerating means for moving the apparatus thereby aerating and homogenizing the microorganisms in culture (FIG. 6B).
Figure 6B:
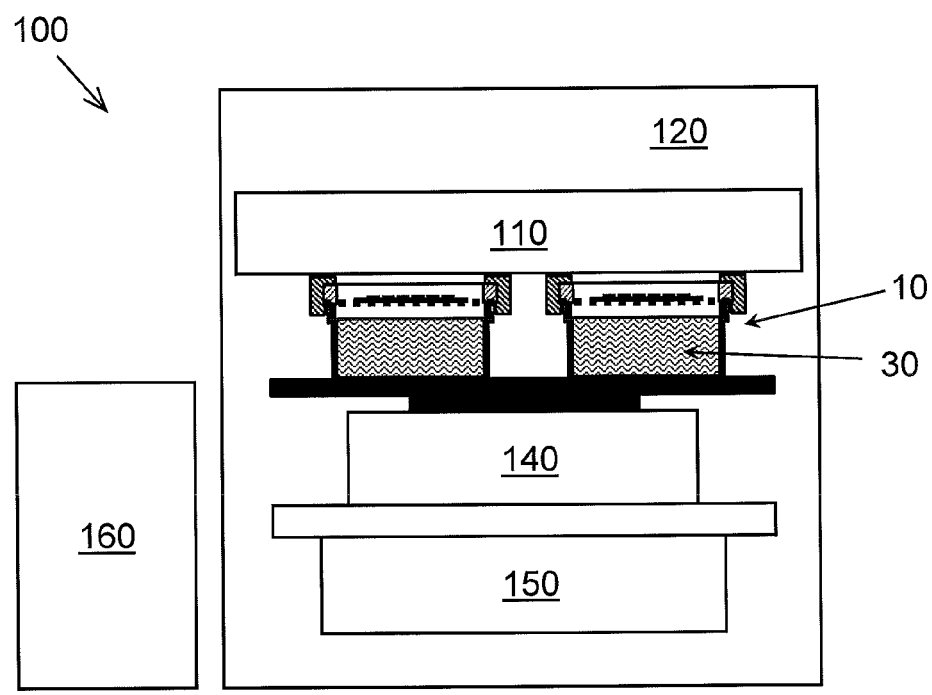

As shown in FIG. 6, the instant apparatus can be a component of an integrated system 100 in which a visual imaging means 110 (e.g., a scanner) is housed in an incubator or growth chamber 120 to maintain the microorganisms at a particular temperature. In the system 100 depicted in FIG. 6A, retractable rack 130 holds apparatus 10, wherein rack 130 can extend when apparatus 10 is to be loaded and retract to a resting position on the bed of the visual imaging means 110 after loading. System 100 can further contain aerating means 140 to agitate apparatus 10, wherein lifting means 150 raises and lowers aerating means 140 to position apparatus 10 adjacent to visual imaging means 110 (see FIG. 6B). Aerating means 140 can be a conventional rocker or shaker which agitates apparatus 10 at low amplitude and frequency to keep the contents therein aerated and homogeneous. System 100 can be driven by software on computer 160, which would register the time at which each apparatus 10 was loaded, drive visual imaging means 110 and process the images, perform data analysis on the color changes occurring during incubation, and output answers such as presence or absence of particular microorganisms and, when particular microorganism are present in the sample, identify the species and strain.

To provide data analysis, the instant apparatus can be combined with standard chemometric statistical analyses (e.g., principal component analysis, hierarchal cluster analysis, and linear discriminant analysis), an artificial neural network (ANN), or other pattern recognition algorithms to correlate dye color changes to various analytes and bacteria species.

Figure 7:
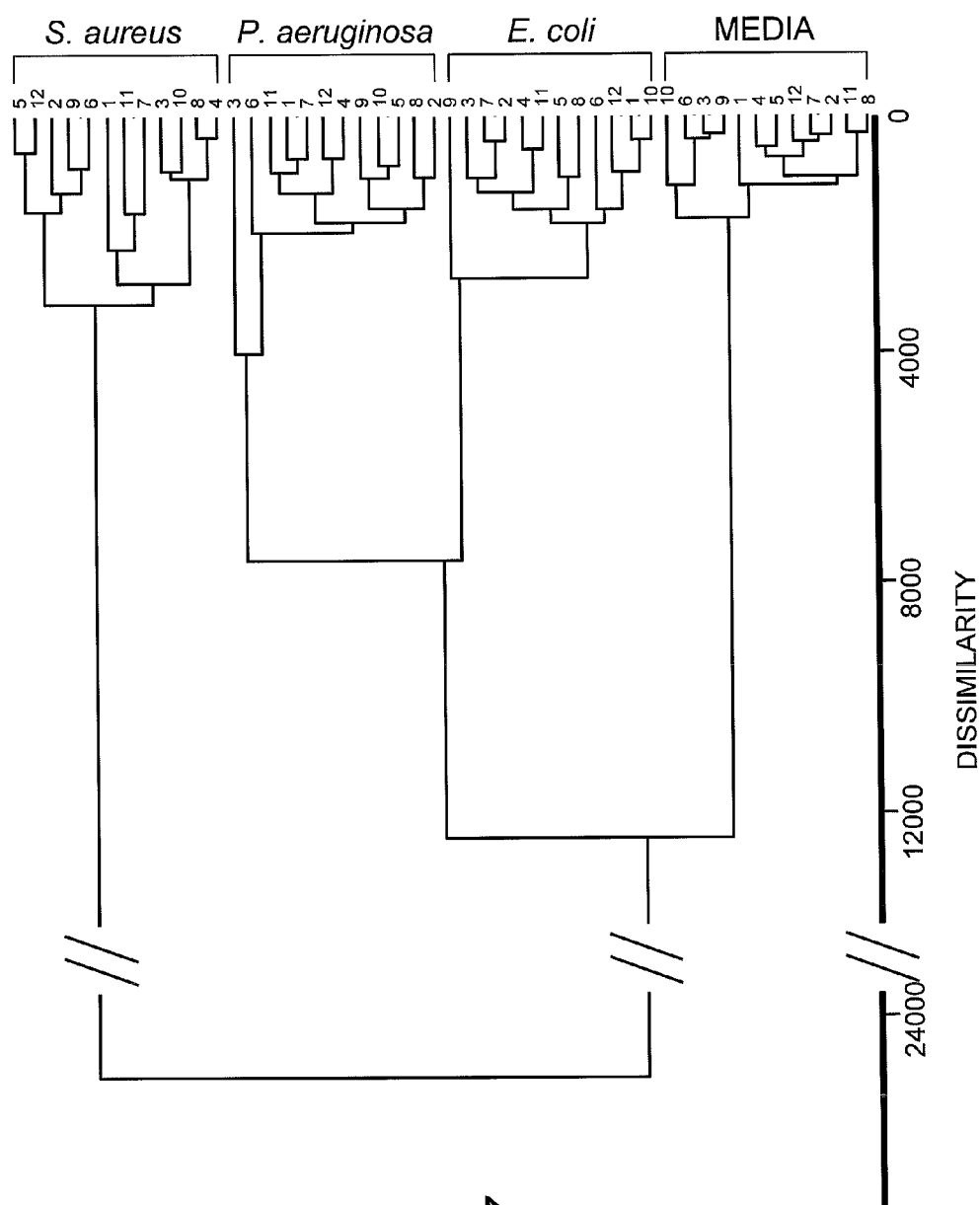
FIG. 7 shows the classification of several species of bacteria (*Staphylococcus aureus, Pseudomonas aeruginosa*, and *Escherichia coli*) using hierarchical cluster analysis.

There is extensive classification information in the temporal or kinetic response of individual dyes as microorganisms grow and undergo changes in metabolism. An example of this behavior is shown in FIG. 7, which charts the color changes of several dye spots exposed to the headspace of a growing culture of microorganisms. Several dye spots undergo reversible color change and the rate of response varies for different dyes. This pattern is different and unique for each species and strain of microorganism.

These temporal color changes can be analyzed using principal component analysis (PCA) to provide bacteria classification and/or identification. PCA determines the number of meaningful, independent dimensions probed by an apparatus of the invention and creates a new coordinate space defined by these dimensions. This space is referred to as "PCA space." Each bacteria species is represented by coordinates in PCA space. Vectors from incoming samples, i.e., unknown microorganisms, are projected onto this new coordinate space and the distance between the unknown vector and the various microorganism vectors in the training set are calculated. The result is a numerical "probability of classification" as each type of microorganism used to build the training set.

The instant array probes a much wider range of chemical interactions than do prior art array sensors, thus the dispersion of the instant calorimetric sensing element is increased over prior art sensing elements. It is this increased dimensionality that permits the discrimination among very closely related compounds, e.g., decylamine versus undecylamine in PCA space.

In hierarchical cluster analysis, the three color channels corresponding to each dye channel can be thought of as vectors in n-dimensional space, where n=3 * N (3 color channels per each of N spots). Hierarchical cluster analysis on the composite n-dimensional vectors at either a single time point or "time stacked" over multiple time points partitions the data into clusters, with each cluster containing all samples of a given microorganism species without cross-classification. As shown in FIG. 7, several species of microorganisms were successfully classified using hierarchical cluster analysis.

Figure 8:
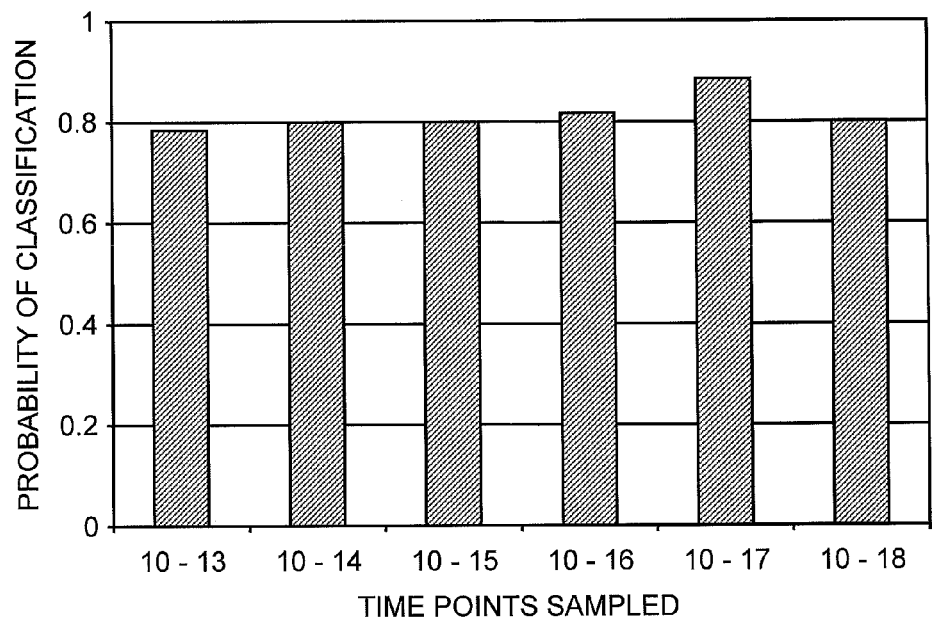
FIG. 8 shows results of linear discriminant analysis for multiple strains of *E. coli*.

A third method, linear discriminant analysis, operates on a training set of data to define a new n-dimensional vector space in which the coordinates are selected so as to minimize the distance between matching vectors (same microorganism species) and maximize the distance between dissimilar vectors (different microorganisms species). Vectors from incoming samples, i.e., unknown microorganisms, are projected onto this new coordinate space and the distance between unknown vector and the various microorganism vectors in the training set are calculated. The result is a numerical "probability of classification" as each type of microorganism used to build the training set. An example of linear discriminant analysis used to classify different strains of $E.\ coli$ is shown in FIG. 8.

By way of further illustration, ANN is an information processing system that functions similar to the way the brain and nervous system process information (Tuang, et al. (1999) *FEMS Microbiol. Lett.* 177: 249-256). The ANN is trained for the analysis and then tested to validate the method. In the training process, the ANN is configured for pattern recognition, data classification, and forecasting. Commercial software programs are available for this type of data analysis. To illustrate, a standardized set of data from an array of dyes exposed to ammonia serves as the input vector. The desired output vector is the classification of ammonia (e.g., produced by Helicobacter), "0" for no ammonia (i.e., no Helicobacter) and "1" for ammonia (i.e., Helicobacter). Training is accomplished by using the standardized data set and associating the input or signature with the desired output or classification. The program compares the data and computes network output with the desired output until an acceptable level of recognition is achieved.

Using such analysis, the instant apparatus can be used for detecting and identifying any microorganism for the purposes of, e.g., diagnosing an infection or detecting a microbial contaminant. Bacterial infections emit specific analytes. The classic diagnosis of strep throat was made by smelling the breath of the patient. Many disease states are associated with distinctive aromas, and the detection of biomarkers represents a fundamental window on the internal functioning of the body (Pavlou, et al. (2000) *Biosensors & Bioelectronics* 15:333-342). The field of gas chromatography has extensively studied the volatile chemicals emitted from microorganisms, and it is clear that different species, even strains with small genetic differences, emit a distinct profile of enzymatic products in the form of volatile organic compounds such as amines, sulfides, and fatty acids (Zechman & Labows (1984) *Can. J. Microbiol.* 31:232-237). The analytes emitted from various microorganisms have been studied in some detail. For example, $E.\ coli$ emits acetic acid when grown in a glucose rich media and ammonia and amines in a protein rich media. Pseudomonads produce alcohols, ketones, and amines, whereas $S.\ aureus$ emits amines, sulfides, and alkenes. These analytes can accumulate to substantial levels, allowing for detection with a cross-responsive sensor in the headspace above the microorganisms or within the growth media itself. The instant apparatus utilizes this fact to detect and identify several bacterial species, including *Escherichia coli, Pseudomonas aeruginosa, Staphylococcus aureus, Streptococcus pyogenes, Staphylococcus epidermidis, Staphylococcus sciuri*, and *Moraxella (Brauhamella) catarrhalis*.

The instant apparatus is useful over the prior art in that changes in the colorimetric sensing element due to microbial metabolism (e.g., increases or decreases in a gaseous compound due to metabolism) are detected in the atmosphere over the growth medium or dissolved in the growth medium; measurements can be made from outside the transparent wall of the container without having to violate the integrity of the container because the sensor is affixed to the interior surface of the container. The external measurements can be made by visual inspection or with an instrument that measures spectroscopic, transmission or reflectance responses, or by image capture; opaque/colored or fluorescent components in the specimen do not interfere with the ability to detect changes or the measurement of those changes; and a plurality of chemoresponsive dyes provides the detection, quantitation, and identification of one or more microorganisms present in the specimen.

Given such advantages, the present invention is also a method for detecting, quantifying and/or identifying a microorganism in a sample. The method involves depositing a sample suspected of containing a microorganism on the medium of the apparatus of the present invention and monitoring changes of the sensing element. In some embodiments, changes include spectroscopic, transmission or reflectance responses of the plurality of chemoresponsive dyes, wherein the detected responses are indicative of the presence and identity of the microorganism.

The sample suspected of containing a microorganism can be a fluid, semi-fluid, or solid sample from a biological or environmental source. Sample can include, e.g., a food item, blood, semen, sputum, mucous, feces, or other bodily discharge as well as a soil or water sample. In the instant method, the sample can be introduced onto or into the medium using any conventional means including spreading the sample across the medium with a glass rod or inoculation loop and injection of liquid with a needle and syringe. The apparatus is then incubated, promoting the growth of microorganism colonies. Dyes of the calorimetric sensing element located in the medium or the headspace of the microorganisms undergo detectable changes and, upon manual or automatic inspection of the array, the presence and identity of microorganism(s) in the sample is determined.

If the calorimetric sensing element is inspected automatically, a system is provided which performs three main functions: incubation of the apparatus, image acquisition/capture, and image processing. The system provides a controlled environment for incubating and promoting growth of microorganisms, which can include a heater if incubation is to take place at an elevated temperature from ambient (though an elevated temperature is not necessary in all situations). Upon adding the sample to the medium of the apparatus, the apparatus is placed in the incubator where it is subsequently sensed/observed by a visual imaging means for image acquisition/capture (e.g., a camera or scanner) during the incubation period. Images of the calorimetric sensing element can be captured at regular predetermined intervals and subsequently analyzed using one or more image processing techniques and algorithms to determine the presence and identity of one or more microorganisms on or in the medium.

As will be appreciated by the skilled artisan, the apparatus and the method of the instant invention can be employed in the detection and identification of a variety of microorganisms. Identification can be on the basis of whether a bacterium is Gram positive or Gram negative, or alternatively, identification of particular genera, species or strains can be achieved. The instant apparatus and method finds application in the detection of the presence or absence of numerous bacteria including, but not limited to, *Bacillus anthracis, Bordetella pertussis, Clostridium botulinum, C. tetani, Corynebacterium diphtheriae, Escherichia coli, Moraxella (Brauhamella) catarrhalis, Pseudomonas aeruginosa, Shigella* spp., *Staphylococcus aureus, Streptococcus pneumoniae, S. pyogenes,* and *Vibrio cholerae*; fungi such as *Microsporum* sp., *Trichophyton* sp., *Epidermophyton* sp., *Sporothrix schenckii, Wangiella dermatitidis, Pseudallescheria boydii, Madurella grisea, Histoplasma capsulatum, Blastomyces dermatitidis, Coccidioides immitis, Cryptococcus neoformans, Aspergillus fumigatus, Aspergillus niger*, and *Candida albicans* as well as protozoa and other parasitic microorganisms. Beneficial and detrimental microorganisms from food, soil, or water samples can also be detected, quantified and identified.

The instant apparatus can be provided to a user in a kit. For example, in embodiments pertaining Lo a Petri dish-type apparatus, the kit can include the bottom of the Petri dish containing the colorimetric sensing element and retainer means already in place with the entire assembly in a hermetic pouch. The other half of the Petri dish containing the medium can be in a separate pouch. When the device is to be used to detect, quantify or identify one or more microorganisms in a sample, the sample in question is deposited or smeared on the medium and the two halves of the apparatus are brought together or otherwise sealed to form the assembled apparatus seen in FIGS. 1B and 1C. The sealed apparatus is then placed on an imaging platform for monitoring and analysis. In embodiments pertaining to a bottle-shaped configuration, the kit can include the bottle with the sensing element and medium already in the bottle. The kit of the invention can also contain other components such as sterile water for diluting the sample, instructions for using the apparatus as well as controls (e.g., a sample of a known concentration of a particular microorganism) and examples of array data indicative of a particular microorganism.

The invention is described in greater detail by the following non-limiting examples.

EXAMPLE 1

Materials

With the exception of the colorimetric sensing elements, all other materials were obtained from the following sources. BACTO™ tryptic soy broth and columbia anaerobic sheep blood agar plates were purchased from Fisher Scientific, Inc (Hampton, N.H.). Sheep serum (S2263) was purchased from Sigma-Aldrich (St. Louis, Mo.). The type of media used for these experiments was chosen because it contains a food source for all of the bacteria studied and all of the species were known to grow on blood agar. Also, it was desirable to develop a system that could be used universally for sensing of all types of volatile bacterial metabolites. Bacteria were purchased from American Type Culture Collection (ATCC, (Manassas, Va.). All materials were used as received and bacteria cultures were stored at −70° C. until used. All UV-vis measurements were carried out at 600 nm against an appropriate blank.

*Escherichia coli* is a gram-negative bacterium that grows on a variety of agar media with an optimal temperature range between 30° C. and 37° C. Colonies on nutrient or blood agar are cream to tan in color, circular, and smooth. The bacterium catabolizes glucose and other carbohydrates found in the media to form acids and "gases" (Wistreich (1999) *Microbiology Perspectives, A Photographic Survey of the Microbial World*; Prentice Hall: Upper Saddle River, N.J.). The most common diseases caused by *E. coli* are gastroenteritis, diarrhea, and urinary tract infections. Isolation and biochemical testing are the conventional approaches used for identification. In particular, specific, selective, and differential media and immunologic tests such as the particle agglutination procedure are conventionally used for the identification of *E. coli* 0157:H7 strains.

*Pseudomonas aeruginosa* is a gram-negative, Bio Safety Level II bacterium that grows best at 37° C. It oxidizes glucose to carboxylic acids but does not produce acid from disaccharides such as lactose. Colonies are large and translucent with irregular edges, and usually appear within 24 to 48 hours. *P. aeruginosa* is an opportunistic pathogen which colonizes and invades injured epithelial surfaces. 75% of all intensive care units patients are colonized by this pathogen. Common diseases caused by this pathogen include pneumonia, chronic respiratory infections, and bacterial meningitis.

Treatment of *P. aeruginosa* is difficult due to its resistance to antibiotics. Most strains of *P. aeruginosa* are conventionally identified on the basis of their characteristic grape-like odor, colonial morphology, and the production of a water-soluble blue pigment, pyocyanin (Campa, et al, Ed. (1993) *Pseudomonas aeruginosa as an Opportunistic Pathogen*; Plenum Press: New York).

*Staphylococcus aureus* is a gram-positive, Bio Safety Level II bacterium which grows best between 30° C. and 37° C. Colonies are usually opaque, smooth, circular, and yellow or sometimes yellow-orange. *S. aureus* is catalase positive and oxidase negative. Several key characteristics of *S. aureus* have been conventionally used to identify the organism and distinguish it from others. These include fermentation of mannitol on mannitol-salt agar, DNAse production, and a positive coagulase test. On average 33% of healthy individuals carry *S. aureus* (A. L. Honeyman & Bendinelli, Ed. (2001) *Staphylococcus aureus Infection and Disease*; Kluwer Academic/Plenum Publishers: New York). This bacterium is known to cause endocarditis, meningitis, pneumonia, and septic arthritis. Commercially available molecular probes and identification systems, immunological tests, and bacterial viruses are used for detection and identification.

*Streptococcus pyogenes* is a gram-positive, Bio Safety Level II bacterium which grows optimally at 37° C. *S. pyogenes* is associated with group A streptococci (GAS) along with *Streptococcus pneumoniae*. Common diseases caused by *S. pyogenes* include strep throat, scarlet fever, pneumonia, and septicemia. Traditional diagnosis relies on a throat culture, in which the bacteria appear as beta-hemolytic colonies on 5% sheep blood agar after 24 to 48 hours.[41]

*Moraxella* (*Brauhamella*) *catarrhalis* is a gram-negative, Bio Safety Level II bacterium that grows on nutrient and blood agar to yield small, circular, convex colonies which are usually grayish white. *M. catarrhalis* exhibits optimal growth between 33° C. to 35° C. *M. catarrhalis* is catalase and oxidase positive and does not produce acid from carbohydrates. This pathogen commonly causes bronchitis, pneumonia, sinusitis, and meningitis. Diagnosis is conventionally obtained by isolation and typical biochemical testing.

EXAMPLE 2

Preparation of Liquid Media

Tryptic soy broth was prepared by dissolving 30 grams of the powdered media into 1 L of purified water. The resulting mixture was divided into 250 mL aliquots and autoclaved at 121° C. for 15 minutes. The bottles were then cooled to room temperature and an aliquot of ~12.5 mL of sheep's serum (prepared beforehand and stored at −70° C. until needed) was added to create an approximate 5% sheep's serum solution by volume. Media bottles that were not used immediately were stored at room temperature without the addition of sheep serum.

EXAMPLE 3

Growth of Bacteria on Solid Media

Before each experiment, a solid media streak plate was prepared from frozen permanent cultures according to conventional methods (Freund & Lewis (1995) *Proc. Natl. Acad. Sci. USA FIELD Publication Date:* 1995 Mar. 28 92:2652-2656) to obtain single colonies for growth in liquid media culture. All plates were incubated at 37° C. until colonies were visible. Streak plates were then wrapped in PARAFILM and stored at 4° C. until further use. Each plate was used for no longer than one month to ensure colony viability, with the following exceptions. Cultures containing *M. catarrhalis* or *S. pyogenes* were prepared weekly because the relevant growth of these organisms on blood agar was less robust than that of other species being tested.

All solid media experiments were conducted at 37° C. in the incubator with a flatbed scanner housed therein. Colorimetric sensing elements were exposed to volatile bacterial metabolites by placing them print side down into the bottom of the appropriate agar plate inoculated with a desired bacterial species. Petri dishes were placed on a flatbed scanner, and images were collected through the clear plastic of the petri dish using CHEMSCAN software.

Two configurations of plates were analyzed. In the first configuration, each 100-mm diameter petri dish contained four individual calorimetric sensing elements and the scanner held six dishes. In the second configuration, 60-mm petri dishes were used which held one colorimetric sensing element and the scanner held twelve petri dishes. To rule out background noise from the response of the agar, the signal arising from inoculated agar at 30 minutes was subtracted from all subsequent time points. Multiple experiments with uninoculated agar revealed that no response to the agar alone was observed after 30 minutes. In addition, control experiments were conducted in which the agar was inoculated with liquid media that contained no bacteria. No signal above that of the agar plate was detected for uninoculated liquid media.

Volatile bacterial metabolite experiments were conducted for at least a 12-hour period with data acquisition occurring at least every 30 minutes. Color change values for the calorimetric sensing elements for all experiments were determined using a customized software package, CHEMEYE™ (Chem-Sensing, Inc.). Digital data was compiled into a database containing each trial run. Chemometric analysis of this database was performed using commercially available software.

The following steps were taken to prepare bacterial species for each experiment. Approximately 5 mL of the appropriate liquid media was inoculated with a single colony of a desired bacteria species from the streak plates. The liquid culture was allowed to grow overnight in a water bath shaker at 37° C. The optical density of the culture was subsequently measured and the solution was diluted to the desired optical density (depending on the growth rate of the species) in either 5 or 10 mL of fresh liquid media. The bacteria were then allowed to grow until the start of the experiments (usually 4 hours). A final optical density measurement was made immediately prior to the start of the volatile bacterial metabolite sensing experiment, the concentration was adjusted a final time, and an appropriate volume of the bacterial culture was spread onto the appropriate agar plate for exposure to colorimetric sensing elements.

Colorimetric sensing elements in inoculated and sealed petri dishes were imaged at regular time intervals post-inoculation. The imaging system employed possessed the ability to collect spatially resolved data so that all of the spots in the calorimetric sensing elements could be individually imaged or addressed and the color of each spot could be individually determined.

EXAMPLE 4

Limits of Detection

For the purposes of the instant apparatus, limit of detection is defined as the smallest number of bacteria that can be detected by colorimetric sensing elements positioned in the headspace of the bacteria. The limit of detection was studied by inoculating tryptic soy agar in petri dishes with a range of colony forming units (cfu) of E. coli. The petri dish was then closed with the calorimetric sensing element in the headspace of the growing bacteria, and the color of the calorimetric sensing element was monitored throughout the growth of the bacteria. The number of colony forming units for each inoculation was determined by counting the visible colonies on each plate at the end of the sensing experiment. Multiple experiments were performed at cfu loadings from 5 cfu to $10^5$ cfu. A typical calorimetric sensing element response pattern and the time needed to detect representative cfu loadings are shown in FIG. 9.

Figure 9:
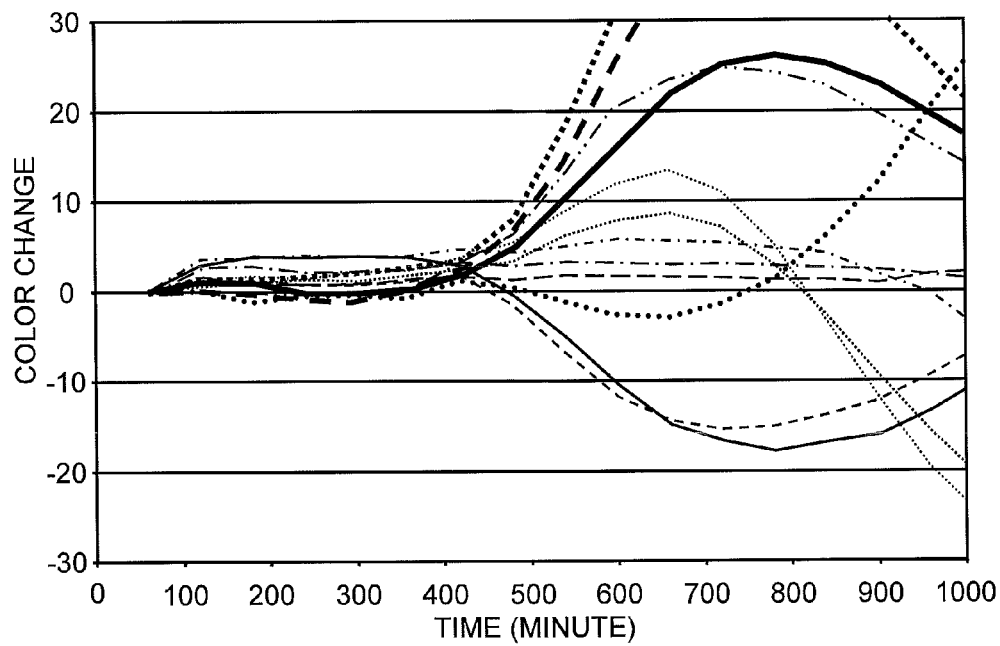
FIG. 9 shows the response of select color channels during the growth of 1020 cfu of *E. coli*.
Figure 10:
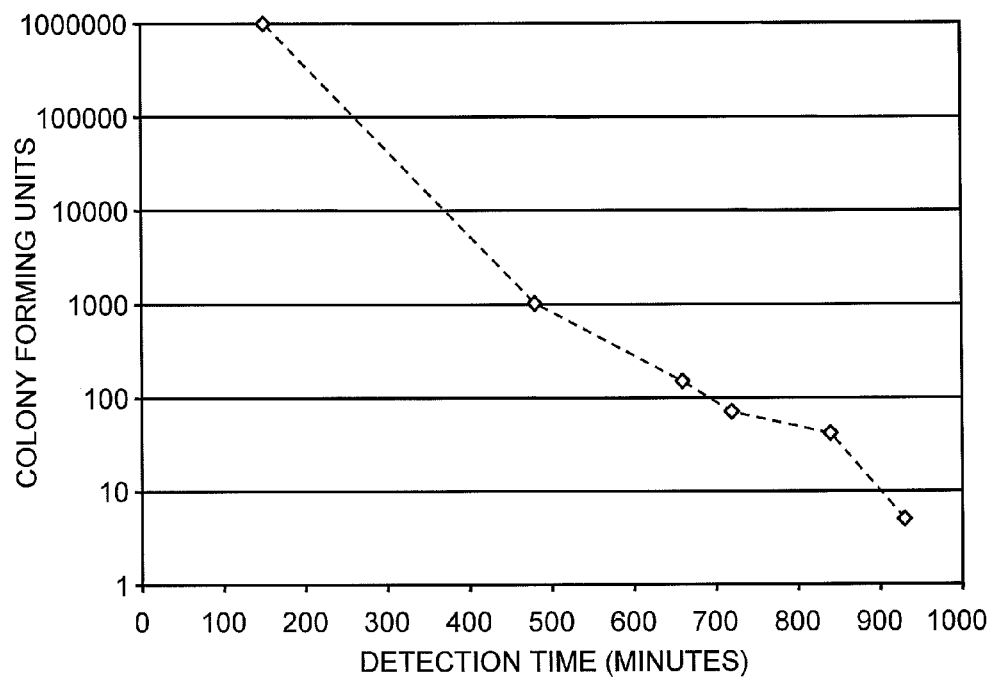
FIG. 10 shows the detection times for representative loadings of *E. coli*.

FIG. 10 shows that time needed to detect an inoculum of 1020 cfu E. coli is approximately 480 minutes (as shown in FIG. 9). The color change curves resulting from lower bacterial loadings contain similar features at and after the time of detection and differ only in the duration of time needed to reach that point. One of the lowest detectable cfu counts measured was 5 cfu, wherein this loading gave detectable signal at 930 minutes.

EXAMPLE 5

Monitoring Bacterial Metabolism

Many bacteria are known to follow several metabolic pathways to yield specific metabolites. When presented with a variety of media sources, most bacteria will consume all of one food type then continue on to the next. For example, when presented with a mixture of glucose and lactose, E. coli will consume the glucose first, and subsequently consume the lactose only when all the glucose is gone.

To demonstrate that a calorimetric sensing element can detect these shifts, the change in RGB values was plotted as a function of time for high loadings of bacteria growing on tryptic soy agar with 5% sheep blood. The calorimetric sensing element allows for the monitoring of the growth stage as well as any changes in emitted metabolites during growth. Therefore, changes in RGB were monitored for E. coli, P. aeruginosa, S. aureus, S. pyogenes, and M. catarrhalis as a function of time. All graphs appeared somewhat similar with large changes in RGB occurring at the ~270 minute mark. Some pronounced shifts were observed in both the E. coli and M. catarrhalis plots, in which some RGB values initially became more negative, and then at ~420 minutes increased again. It is believed that this behavior was caused by the depletion of glucose in the medium and subsequent switch to protein as a source of nutrients. Initial calorimetric sensing element responses corresponded to the production of acid from the growing bacteria. Upon cessation of acidification, a reversal in color change direction was observed. This may correspond to the production of basic analytes, such as ammonia and various amines, as the protein in the medium was metabolized. Similar shifts were seen for several other bacteria, to include S. aureus and S. pyogenes.

EXAMPLE 6

Solid Media Growth Curves

The number of bacteria present and producing volatile metabolites at any given time is directly related to how quickly the bacteria double. Since bacteria grow exponentially, the number of bacteria present after a specific growth time is dependent on the initial number of bacteria present in the culture. Each new generation of cells produced leads to double the previous amount. The equation to determine the number of bacteria present at any given time during growth is given below:

$$\int_{t_i}^{t_f} t N_o 2^{t/t_d} dt$$

where $t_f$ is the final time, $t_i$ is the initial time, t is time, $N_o$ is initial number of bacteria and $t_d$ is doubling time. The doubling time ($t_d$) is dependent on the bacteria and the media source, as well as the environmental conditions.

Conventional growth curves are determined by measuring the optical density of bacteria grown in liquid culture. However, there is no direct method of obtaining growth curves of bacteria grown on solid media. Traditional methods for monitoring growth of bacteria grown on solid media require the use a special soft agar. An initial amount of bacteria, determined by measuring the optical density, is plated as a lawn and allowed to grow for a desired period of time, upon which the bacteria are scraped off the plate and dissolved in fresh liquid medium. UV/VIS spectroscopy is then performed to determine O.D. and the number of bacteria present is then back calculated. A separate agar plate is required for each time point used in determining the growth curves. As such, this method is time consuming and prone to error and human variability.

Advantageously, the response of calorimetric sensing elements to growing bacterial cultures is an initial sharp increase in signal and then, after a time that varies with the species being monitored, reaches a generally constant level. A plot of this change with time yields a growth curve. The change in colorimetric sensing element response is defined as the total minimum variance which is the normalized Euclidean distance of all 108 RGB values for each time point examined during bacterial growth. In other words, it is a measure of distance between time points in 108-dimensional space for a calorimetric sensing element that contains 36 spots. Using changes in colorimetric sensing element response to monitor growth of E. coli on tryptic soy agar with 5% sheep blood, it was found that the growth curve observed on solid media exhibits features found in conventional liquid growth curves; a lag phase followed by an exponential growth phase and a stationary phase.

Figure 11:
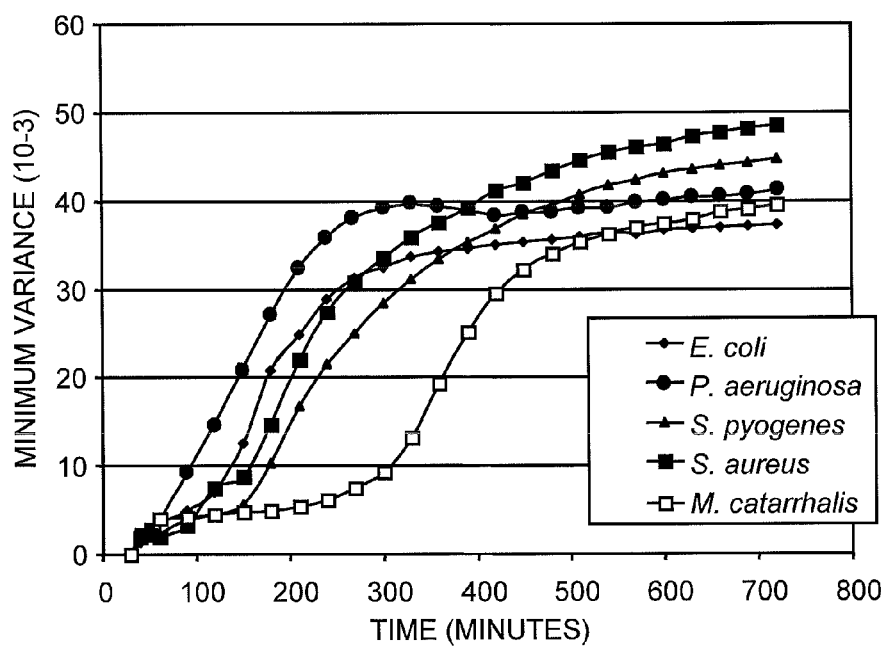
FIG. 11 shows growth curves obtained with calorimetric sensing elements for *E. coli, P. aeruginosa, S. pyogenes, S. aureus*, and *M. catarrhalis* on solid tryptic soy agar with 5% sheep blood.

All bacteria studied have similar growth curves when grown on the same solid media. As shown in FIG. 11, the general shape of the curve is the same for all bacteria tested, with growth rate being species-dependent. These growth curves resemble those corresponding to growth in liquid media.

EXAMPLE 7

Colorimetric Sensing elements and Liquid/Blood Culturing

Sepsis is typically associated with blood bacteria concentrations of less than 10 colony forming units (cfu) per mL of blood. This concentration does not readily allow for the identification of the bacteria using non-DNA based techniques. As such, the bacteria are generally grown, or cultured, to provide a sufficient number of bacteria for identification.

The blood culturing process involves obtaining blood samples from the patient suspected of being septic, and injecting each sample into a dedicated blood culture bottle, which contains a liquid medium that supports the growth of the bacteria, a gas tight seal that prevents analytes generated by the growing bacteria from escaping and allowing for pressure to develop in the bottle, and a sensor that indicates whether or not bacteria are present. Blood culture bottles are typically interfaced to a monitoring incubator that maintains a temperature of 37° C. and reads the sensor to alert the user when the presence of bacteria has been verified. A bottle that does not register positive for bacteria within 5 days is typically considered to be negative for bacteria.

Conventional blood culturing sensing systems employ a $CO_2$ sensor, either colorimetric or fluorescent in nature, or a pressure sensor. However, $CO_2$ is inherently only weakly reactive relative to many other gases and thus greater concentrations of $CO_2$ are required to register a change in color or fluorescence. By employing the instant colorimetric sensing element in a blood/liquid culture system, more reactive analytes can be and are detected, thereby decreasing the time needed to detect bacteria in a blood culture bottle. Moreover, whereas conventional blood culture systems are designed only for bacterial detection, the instant colorimetric sensing element can also readily identify the species of bacteria based on the analytes evolved during growth. In particular, the instant colorimetric sensing element is sensitive to bacterial analytes such as amines and carboxylic acids at sub part per million (ppm) levels; sulfides and thiols on ppm levels; $CO_2$ at sub ten ppm levels; and aldehydes and alcohols, though at higher concentrations.

To demonstrate the use of the instant apparatus in blood culturing, E. coli was grown in liquid media overnight and diluted to the desired optical density prior to use. A mixture of 20% human blood and 80% liquid media were then added to the container, in this case a bottle, followed by the appropriate volume of the bacterial solution to attain the desired initial number of bacteria in the blood culture bottle. Blood was freshly drawn from human subjects and used within 10 minutes after draw. Subsequently, the cap was placed on the bottle, the bottle loaded onto a shaking and imagining platform, and the zero-point or baseline image collected. After several experiments, it was observed that a signal arises from the media itself but this signal reached a steady state after thirty minutes. As such, all blood culture data is presented with the thirty minute point serving as the baseline.

Figure 12:
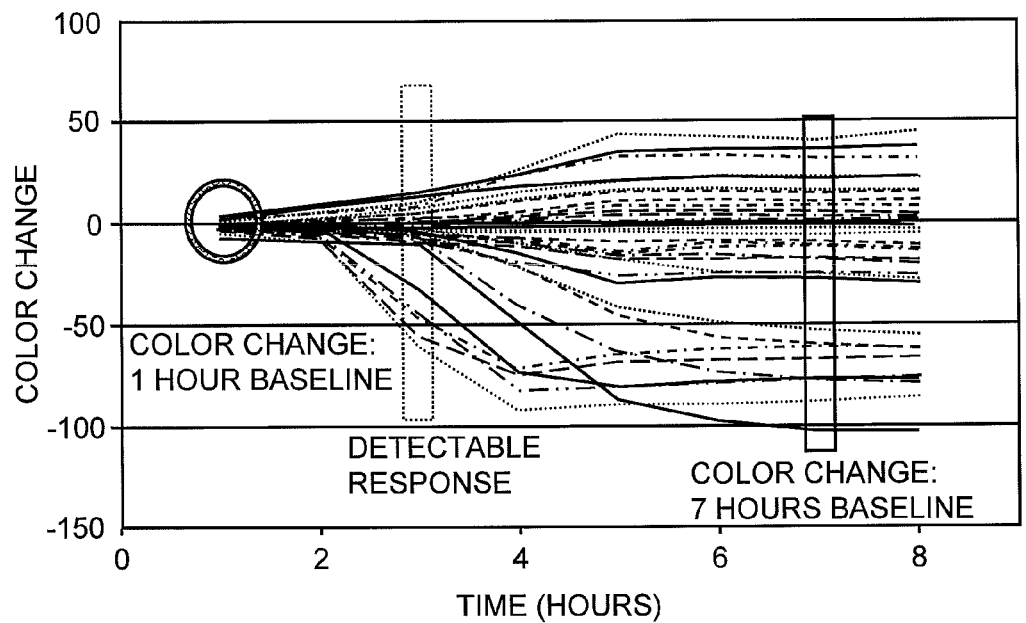
FIG. 12 shows a sample of data collected from blood culture experiments, wherein each line represents a different color channel.

FIG. 12 shows representative results from a single blood culture experiment. Each colored line in the graph represents a single color channel, where "color channel" is defined as the individual Red, Green and Blue components of each dye spot. For instance, the red component of dye spot 12 is termed color channel R12, the green component of dye spot 12 is color channel G12, etc. Definite signal-above-baseline was observable by the three-hour point.

To examine the signal arising from exposure of the colorimetric sensing element to liquid medium only, the calorimetric sensing element was exposed to pure medium in the absence of blood and bacteria. In three separate experiments, which monitored calorimetric changes over a seven-hour period, all calorimetric signal array changes were in the range of −20 to +20, with little fluctuation in signal throughout the course of the experiment.

Given that human blood cells can remain vital and produce analytes when incubated in liquid medium of the sort used herein, colorimetric signal array changes arising from human blood and medium alone were determined in the absence of bacteria. The results from nine separate experiments indicated that the signal arising from blood/media mixtures, while in some cases larger than that arising from pure media alone, did not interfere with the detection of bacteria.

The detection of E. coli growing in 20% human blood and 80% medium was subsequently analyzed. Colorimetric sensing element signal resulting from "high" loadings of E. coli in the blood/media mixture was determined. High loadings were defined as an initial concentration in the blood culture bottle of at least $10^4$ cfu/mL as determined by optical density measurements of the liquid bacterial culture prior to inoculating the blood/media. Separate experiments were conducted with media which support aerobic microorganisms and anaerobic microorganisms. While the experiments were not conducted under anaerobic conditions, a clear difference between the signals arising from bacteria grown in these two media was apparent. In all cases the bacteria was easily detected within three hours after inoculation of the blood/media mixture.

In addition to "high" loading, calorimetric sensing element signal resulting from "low" loadings of E. coli was also determined. Low loadings were defined as an initial cell concentrations ranging from 500 cfu/mL to 4000 cfu/mL. The results of this analysis indicated that in all cases the signal was substantially stronger than that observed from blood/media alone. Furthermore, signal from low loadings differed from that of high loadings in two ways; longer time for detection and a decrease in the negative spike. The data at low loadings of E. coli represented a close approximation of an expanded version of the data obtained with high loadings of E. coli in which similar features occurred but at later times.

Figure 13:
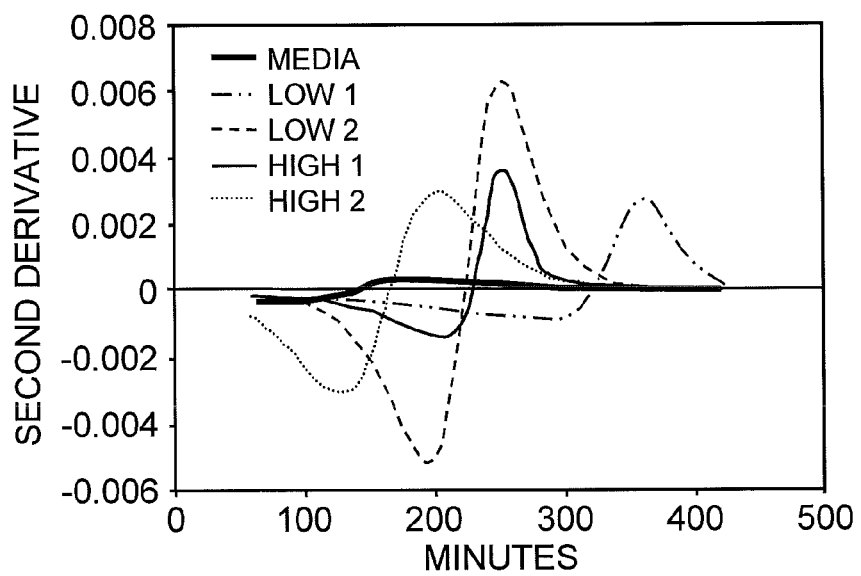
FIG. 13 shows the second derivative of color channel B28, as a function of time, from colorimetric sensing element signal arising from low loadings of *E. coli* (i.e., initial cell concentrations of 500 cfu/mL to 4000 cfu/mL).

To define the detection of bacteria over signal from blood/media, a mathematical formalism was developed. In other words, a rigorous method of analyzing the colorimetric sensing element signal was created to yield a yes or no answer that did not depend upon visual analysis of a graph. Analysis of blood/media as compared to low load or high load cultures was conducted. In this analysis, the signal from blood/media resembled that of a low load culture and it was difficult to discern by visual examination of the graphs whether the low load culture contained bacteria or not (the initial concentration of cells in low load was 200 cfu/mL as measured by optical density followed by serial dilutions). As such, to definitively determine the presence of bacteria in the low load culture, a closer examination of color channels G22 and B28 was carried out, as G22 and B28 exhibited a steady upward increase in several of the blood/media instances but showed structure in the case of samples inoculated with bacteria. This structure was most apparent when the second derivative of each of the two lines was plotted as a function of time (FIG. 13). The second derivatives were calculated by first fitting each line to a sigmoid, a twice continuously differentiable function that closely approximates the actual data. The second derivative of "media" (the blood/media mixture) was essentially flat and never reached a value greater than ±0.0003. In contrast to the flat nature of the blood/media curve, all other samples exhibited a second derivative greater than ±0.003, an order of magnitude greater (FIG. 13).

Figure 14:
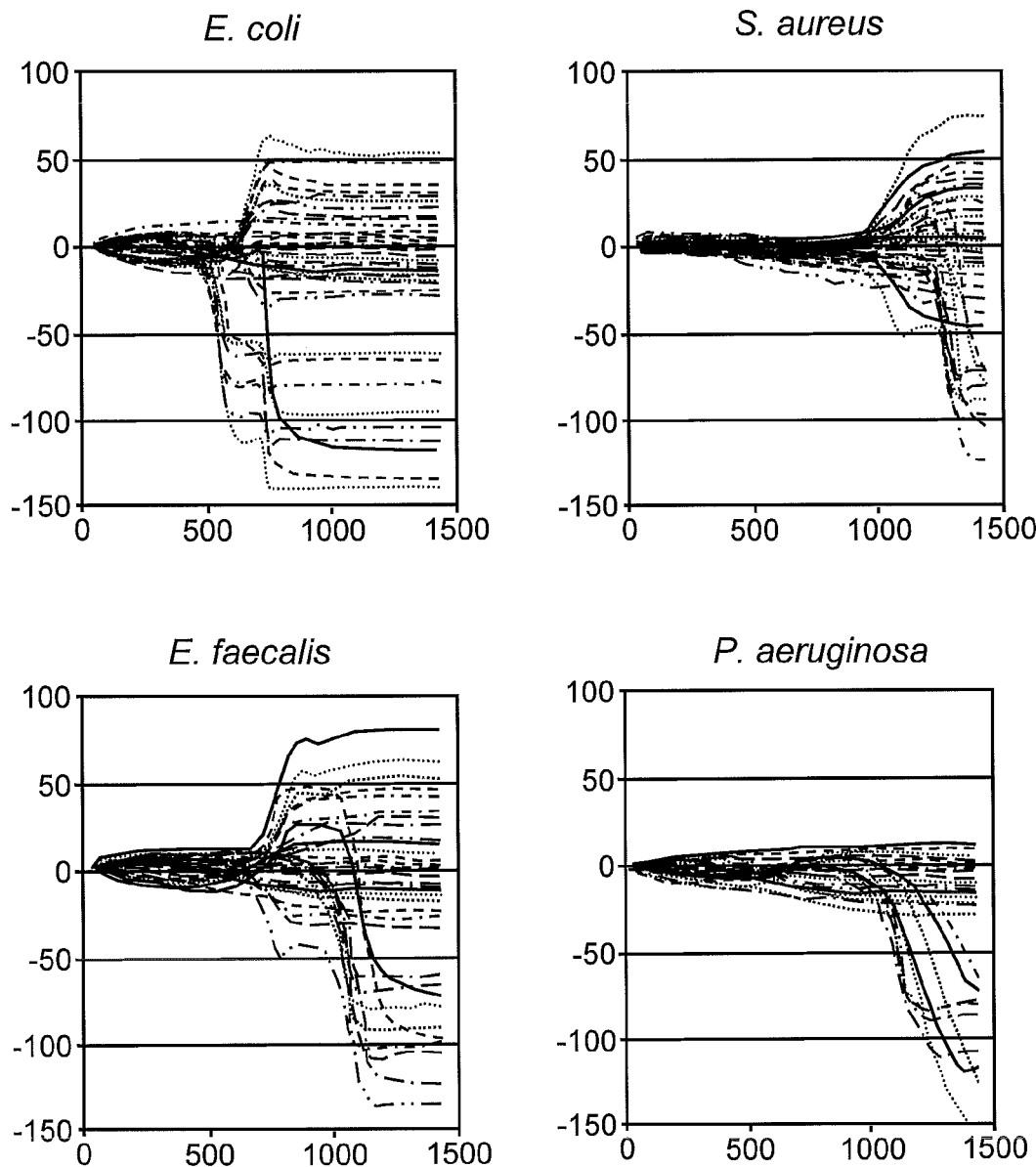
FIG. 14 depicts colorimetric sensing element response patterns for *E. coli, S. aureus, E. faecalis*, and *P. aeruginosa* grown in blood culture.

To further demonstrate that the apparatus is applicable to the identification of bacteria growing in liquid media, a colorimetric sensing element was placed in bottles inoculated with bacteria loadings comparable to those observed in clinical samples: between 20 and 80 cfu per bottle. This corresponds to 2 to 8 cfu/mL in blood drawn from a septic patient. As shown in FIG. 14, each of the bacteria (i.e., E coli, S. aureus, E. faecalis, and P. aeruginosa) generated a unique colorimetric sensing element response pattern that clearly identified the bacteria.

What is claimed is:

1. An apparatus for detecting, quantifying or identifying a microorganism comprising
   (a) a container with at least one chamber;
   (b) a medium within the chamber of the container, wherein said medium is supplemented with nutrients for supporting growth of a microorganism; and
   (c) at least one colorimetric sensing element placed in, or proximate to, the medium, wherein said sensing element includes a substrate comprising a plurality of chemoresponsive dyes in a predetermined pattern combination, wherein the sensing element comprises at least two different classes of dyes selected from the group of Lewis acid/base dyes, Brnsted acid or base dyes; or zwitterionic solvatochromic dyes, wherein each of said dyes comprises a chromophore and wherein the combination of the dyes have a distinct and direct spectroscopic, transmission, or reflectance response to distinct analytes produced by the microorganism which is indicative of the presence and identity of the microorganism.

2. The apparatus of claim 1, further comprising an air flow means.

3. The apparatus of claim 1, wherein all or a portion of the container is transparent or translucent.

4. The apparatus of claim 1, wherein the colorimetric sensing element is attached to a cap or lid of the container.

5. The apparatus of claim 1, further comprising a second chamber comprising the colorimetric sensing element, wherein the chambers of the apparatus are separated by a gas impermeable barrier.

6. A system for detecting, quantifying or identifying a microorganism comprising the apparatus of claim 1 and a visual imaging means for detecting spectroscopic, transmission or reflectance responses of the plurality of chemoresponsive dyes.

7. The system of claim 6, further comprising one or more of an aerating means, a computer, or a growth chamber.

8. The system of claim 7, wherein the aerating means comprises a shaker or rocker.

9. The system of claim 6, wherein the visual imaging means comprises an imaging spectrograph, fiber optic probes coupled to a spectrograph, scanner, or camera.

10. A kit comprising the apparatus of claim 1.

11. A method for detecting, quantifying or identifying a microorganism comprising depositing a sample suspected of containing a microorganism onto or into the medium of the apparatus of claim 1 and monitoring spectroscopic, transmission or reflectance responses of the plurality of chemoresponsive dyes thereby detecting, quantifying, or identifying the microorganism.

* * * * *